US009061991B2

(12) United States Patent
Asuma et al.

(10) Patent No.: US 9,061,991 B2
(45) Date of Patent: Jun. 23, 2015

(54) METHOD FOR PRODUCING 1-AMINO-1-ALKOXYCARBONYL-2-VINYLCYCLOPROPANE

(75) Inventors: Yuuki Asuma, Kanagawa (JP); Tatsuya Suzuki, Kanagawa (JP); Jun Takehara, Fukuoka (JP); Tsugihiko Hidaka, Fukuoka (JP); Kuniko Asada, Tokyo (JP); Ryoma Miyake, Kanagawa (JP); Yasumasa Dekishima, Kanagawa (JP); Hiroshi Kawabata, Tokyo (JP)

(73) Assignee: API CORPORATION, Tokyo (JP)

( * ) Notice: Subject to any disclaimer, the term of this patent is extended or adjusted under 35 U.S.C. 154(b) by 0 days.

(21) Appl. No.: 13/579,045

(22) PCT Filed: Feb. 16, 2011

(86) PCT No.: PCT/JP2011/053285
§ 371 (c)(1),
(2), (4) Date: Dec. 13, 2012

(87) PCT Pub. No.: WO2011/102388
PCT Pub. Date: Aug. 25, 2011

(65) Prior Publication Data
US 2013/0096339 A1   Apr. 18, 2013

(30) Foreign Application Priority Data
Feb. 16, 2010   (JP) .................................. 2010-031322

(51) Int. Cl.
| | | |
|---|---|---|
| C07C 1/32 | (2006.01) | |
| C07C 13/04 | (2006.01) | |
| C07C 67/343 | (2006.01) | |
| C07B 53/00 | (2006.01) | |
| C07B 57/00 | (2006.01) | |
| C07C 67/313 | (2006.01) | |
| C07C 227/04 | (2006.01) | |
| C07C 227/32 | (2006.01) | |
| C07C 269/02 | (2006.01) | |
| C07C 247/22 | (2006.01) | |
| C12P 41/00 | (2006.01) | |
| C12P 7/62 | (2006.01) | |

(52) U.S. Cl.
CPC .............. *C07C 67/343* (2013.01); *C07B 53/00* (2013.01); *C07B 57/00* (2013.01); *C07C 67/313* (2013.01); *C07C 227/04* (2013.01); *C07C 227/32* (2013.01); *C07C 2101/02* (2013.01); *C07C 269/02* (2013.01); *C07C 247/22* (2013.01); *C07B 2200/07* (2013.01); *C12P 41/005* (2013.01); *C12P 7/62* (2013.01)

(58) Field of Classification Search
CPC ................................... C07C 13/04; C07C 1/32
USPC ....................................................... 560/124
See application file for complete search history.

(56) References Cited

U.S. PATENT DOCUMENTS

| | | | |
|---|---|---|---|
| 4,252,739 | A | 2/1981 | Fayter, Jr. et al. |
| 4,328,168 | A | 5/1982 | Fayter, Jr. |
| 4,713,478 | A | 12/1987 | Fayter, Jr. |
| 6,344,179 | B1 | 2/2002 | Goodman et al. |
| 2005/0040371 | A1 | 2/2005 | Watanabe et al. |
| 2007/0093414 | A1 | 4/2007 | Carini et al. |
| 2009/0292129 | A1 | 11/2009 | Napolitano et al. |

FOREIGN PATENT DOCUMENTS

| | | |
|---|---|---|
| CN | 101379029 A | 3/2009 |
| EP | 25846 A1 | 4/1981 |
| EP | 269109 A2 | 6/1988 |
| EP | 330788 A1 | 9/1989 |
| EP | 330824 A1 | 9/1989 |
| EP | 1986996 A2 | 11/2008 |
| JP | 56-45425 | 4/1981 |
| JP | 01-268634 | 10/1989 |
| JP | 63-150249 | 6/1998 |
| JP | 2005-34025 | 2/2005 |
| JP | 2005-072209 | 3/2005 |
| JP | 2009-525320 | 7/2009 |
| WO | 00/64490 | 11/2000 |
| WO | 2004/094452 | 11/2004 |
| WO | 2007/015824 | 2/2007 |
| WO | 2007/088571 | 8/2007 |
| WO | 2010/041739 | 4/2010 |
| WO | 2011/003063 | 1/2011 |

OTHER PUBLICATIONS

Franzone et al, Synlett (1996), pp. 1067-1070.*
Fliche et al., "Enantioselective Synthesis of (1R,2S) and (1S,2S) Dehydrocoronamic Acids", Synthetic Communications 24(20), 1994, pp. 2873-2876.*
Rancourt et al., "Peptide-Based Inhibitors of the Hepatitis C Virus NS3 Protease: Structure-Activity Relationship at the C-Terminal Position", Journal of Medicinal Chemistry 47(10), 2004, pp. 2511-2522.
Dojin, "Translated by Ito, Kodama, McMurry Yuki Kagaku", (last volume), 4th edition, 1st Print, Apr. 6, 1998, pp. 965-968.

(Continued)

*Primary Examiner* — Kamal Saeed
*Assistant Examiner* — Janet L Coppins
(74) *Attorney, Agent, or Firm* — Greenblum & Bernstein, P.L.C.

(57) ABSTRACT

It is an object of the present invention to provide a novel method for producing (1R,2S)/(1S,2R)-1-amino-1-alkoxycarbonyl-2-vinylcyclopropane which is useful as a synthetic intermediate of therapeutic agents for hepatitis C and a synthetic intermediate thereof. According to the present invention, when a trans-2-butene derivative having a leaving group at each of the 1- and 4-positions is reacted with a malonic ester in the presence of a base, a specific amount of an alkali metal alkoxide or an alkali metal hydride is used as the base, and further a specific amount of a malonic ester is used to produce a cyclopropane diester, and further, chiral or achiral 1-amino-1-alkoxy-carbonyl-2-vinylcyclopropane and a salt thereof are synthesized using the cyclopropane diester.

18 Claims, No Drawings

(56) References Cited

OTHER PUBLICATIONS

Jikken Kagaku Koza, "The Chemical Society of Japan", 27, 4th edition, Maruzen Co., Ltd., May 5, 1991, pp. 418-426.

Search report from International Application No. PCT/JP2011/053285, mail date is Apr. 12, 2011.

Christie et al., "Novel formation and use of a Nicholas carbocation in the synthesis of highly substituted tetrahydrofurans", Chem. Commun., 2004, 2474-2475.

Miura et al., "Indium (III) Salt Promoted Intramolecular Addition of Allylsilanes to Unactivated Alkynes", Synlett 2006, No. 12, pp. 1883-1886.

Miura et al., "Indium (III) Chloride-Promoted Intramolecular Addition of Allylstannanes to Alkynes", J. Org. Chem. 2004, 69, 2427-2430.

Dolle et al., "Synthesis, radiosynthesis and in vivo preliminary evaluation of [$^{11}$C]LBT-999, a selective radioligand for the visualization of the dopamine transporter with PET", Bioorg. Med. Chem. 2006, 14, 1115-1125.

Blanchard et al., "Diethylaluminum Chloride-Amine Complex Mediated Aminolysis of Activated Cyclopropanes", J. Org. Chem. 1986, 51(8), 1372-1374.

Parsons et al., "Diastereoselective Synthesis of Tetrahydrofurans via Palladium(0)-Catalyzed [3 + 2] Cycloaddition of Vinylcyclopropanes and Aldehydes", Org. Lett. 2008, 10(12), 2541-2544.

International Preliminary Report on Patentability and Written Opinion of the Searching Authority for PCT/JP2011/053285, mailed Sep. 27, 2012 with English Translation thereof.

Hosomi et al., "Preparation, Characterization, and Stereochemistry of 2-Methyl-2-silabicyclo[2.2.1]heptane Derivatives," Bull. Chem. Soc. JPN., vol. 56, No. 9, 1983, pp. 2784-2794.

Extended European Search Report from EP 11744674.0, dated Jun. 6, 2013.

Chinese Office Action issued with respect to Chinese Application No. 201180009865.9, mail date is Feb. 13, 2014.

Japanese Office Action issued with respect to Japanese Patent Application No. 2011-508144, mailed Nov. 26, 2013.

Chinese Office Action issued with respect to application No. 201180009865.9, mail date is Dec. 31, 2014.

* cited by examiner

METHOD FOR PRODUCING 1-AMINO-1-ALKOXYCARBONYL-2-VINYLCYCLOPROPANE

TECHNICAL FIELD

The present invention relates to a method for producing (1R,2S)/(1S,2R)-1-amino-1-alkoxycarbonyl-2-vinylcyclopropane and a synthetic intermediate thereof. The (1R,2S)/(1S,2R)-1-amino-1-alkoxycarbonyl-2-vinylcyclopropane produced by the method of the present invention is useful as a synthetic intermediate of therapeutic agents for hepatitis C.

BACKGROUND ART (1R,2S)/(1S,2R)-1-amino-1-ethoxycarbonyl-2-vinylcyclopropane is an intermediate useful for the synthesis of various types of HCV NS3 protease inhibitors and the like, which are currently under development as therapeutic agents for hepatitis C. It is considered that 1,1-di-ethoxycarbonyl-2-vinylcyclopropane and a chiral form of 1-ethoxycarbonyl-2-vinylcyclopropane carboxylic acid are useful as intermediates for synthesizing the (1R,2S)/(1S,2R)-1-amino-1-ethoxycarbonyl-2-vinylcyclopropane.

Patent Document 1 and Example 21 of Patent Document 2 describe that trans-1,4-dibromo-2-butene is allowed to react with diethyl malonate in dichloromethane in the presence of potassium hydroxide (90% flake form) and tricaprylylmethylammonium chloride, so as to obtain 1,1-di-ethoxycarbonyl-2-vinylcyclopropane at a yield of 89%.

In addition, Non Patent Documents 1 to 3 and the like describe a reaction of forming a cyclopropane ring using 1,4-dichloro-2-butene or 1,4-dibromo-2-butene. However, these methods are industrially disadvantageous in terms of yield, and in that dichloromethane that is a halogen compound is used as a solvent and also in that the reaction is a solid-liquid two phase reaction.

PRIOR ART DOCUMENTS

Patent Documents

[Patent Document 1] JP Patent Publication (Kokai) No. 56-45425 A (1981)
[Patent Document 2] U.S. Pat. No. 4,252,739

Non Patent Documents

[Non Patent Document 1] Steven D. R. Christie et al., Chem. Commun., 2004, 2474-2475
[Non Patent Document 2] Katsuhiko Miura et al., SYNLETT 2006, No. 12, pp. 1883-1886
[Non Patent Document 3] Katsuhiko Miura et al., J. Org. Chem. 2004, 69, 2427-2430

DISCLOSURE OF INVENTION

Object to be Solved by the Invention

It is an object to be solved by the present invention to provide a novel method for producing (1R,2S)/(1S,2R)-1-amino-1-alkoxycarbonyl-2-vinylcyclopropane which is useful as a synthetic intermediate of therapeutic agents for hepatitis C and a synthetic intermediate thereof. That is to say, it is the object to be solved by the present invention to provide an industrially applicable method for producing 1-amino-1-alkoxycarbonyl-2-vinylcyclopropane and a synthetic intermediate thereof which are in an achiral form and a chiral form.

Means for Solving the Object

As a result of intensive studies directed towards achieving the aforementioned object, the present inventors have used a specific amount of alkali metal alkoxide or alkali metal hydride as a base and have also used a specific amount of malonic ester, when a trans-2-butene derivative having leaving groups at positions 1 and 4 is allowed to react with such a malonic ester in the presence of a base, so that the inventors have succeeded in synthesizing a vinylcyclopropane ring diester at a high yield, thereby completing the present invention. Moreover, using the thus synthesized compound, the inventors have succeeded in synthesizing 1-amino-1-alkoxycarbonyl-2-vinylcyclopropane and a salt thereof, which are in a chiral form or achiral form, by an industrially applicable method, thereby completing the present invention.

According to the present invention, the following invention is provided.

[1] A method for producing a compound represented by the following formula (4):

[Formula 2]

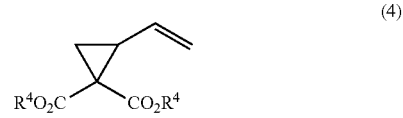

wherein $R^4$ represents an alkyl group containing 1 to 10 carbon atoms, an aralkyl group containing 7 to 20 carbon atoms or an aryl group containing 6 to 12 carbon atoms, each of which may be optionally substituted, wherein the method comprises a step (i) of allowing a compound represented by the following formula (3):

[Formula 1]

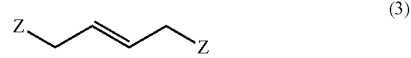

wherein Z represents a halogen atom or $OR^3$, wherein $R^3$ represents an arylsulfonyl group containing 6 to 12 carbon atoms, an alkylsulfonyl group containing 1 to 10 carbon atoms or an aralkylsulfonyl group containing 7 to 20 carbon atoms, each of which may be optionally substituted, to react with a malonic ester in the presence of an alkali metal alkoxide or alkali metal hydride, to produce the compound represented by the formula (4), wherein, in the step (i), the alkali metal alkoxide or alkali metal hydride is used in an amount of 1.5 equivalents or more with respect to 1 equivalent of the compound represented by the above formula (3), and the malonic ester is used in an amount of 1 equivalent or more with respect to 1 equivalent of the alkali metal alkoxide or alkali metal hydride.

[2] The method according to [1], which further comprises, before the step (i), a step (ii) of hydrolyzing, with an acid or a base, a compound represented by the following formula (1):

[Formula 3]

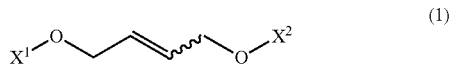

(1)

wherein $X^1$ represents a hydrogen atom or $R^1$, and $X^2$ represents a hydrogen atom or $R^2$, wherein $R^1$ and $R^2$ each independently represent an alkylcarbonyl group containing 2 to 11 carbon atoms, an aralkylcarbonyl group containing 8 to 21 carbon atoms or an arylcarbonyl group containing 7 to 13 carbon atoms, each of which may be optionally substituted, provided that $X^1$ and $X^2$ do not simultaneously represent hydrogen atoms, so as to produce a compound represented by the following formula (2):

[Formula 4]

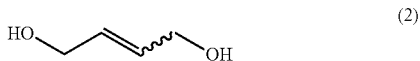

(2)

a step (iii) of allowing the compound represented by the above formula (2), which has been obtained by the above step (ii), to react with a compound represented by $R^3X$ (wherein $R^3$ represents an arylsulfonyl group containing 6 to 12 carbon atoms, an alkylsulfonyl group containing 1 to 10 carbon atoms or an aralkylsulfonyl group containing 7 to 20 carbon atoms, each of which may be optionally substituted; and X represents a halogen atom), so as to produce a compound represented by the following formula (3b):

[Formula 5]

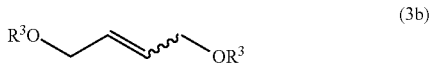

(3b)

wherein $R^3$ represents an arylsulfonyl group containing 6 to 12 carbon atoms, an alkylsulfonyl group containing 1 to 10 carbon atoms or an aralkylsulfonyl group containing 7 to 20 carbon atoms, each of which may be optionally substituted; and a step (iv) of crystallizing the compound represented by the above formula (3b), which has been obtained by the above step (iii), so as to produce a compound represented by the following (3a):

[Formula 6]

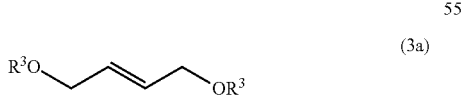

(3a)

wherein $R^3$ represents an arylsulfonyl group containing 6 to 12 carbon atoms, an alkylsulfonyl group containing 1 to 10 carbon atoms or an aralkylsulfonyl group containing 7 to 20 carbon atoms, each of which may be optionally substituted.

[3] The method according to [1] or [2], which comprises a step of purifying the compound represented by the formula (4) after performing the step (i).

[4] A method for producing a compound represented by the following formula (5):

[Formula 8]

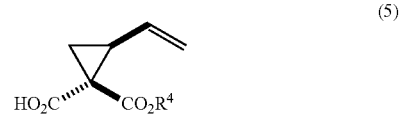

(5)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted, wherein the method comprises:

a step (v) of producing a compound represented by the following formula (4) by the method according to any one of [1] to [3]:

[Formula 7]

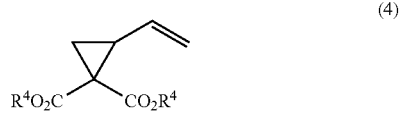

(4)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted; and a step (vi) of subjecting the compound represented by the above formula (4), which has been obtained by the above step (v), to hydrolysis, or to hydrolysis and optical resolution, to produce the compound represented by the formula (5).

[5] The method according to [4], wherein the step (vi) is a step (vi-1) of allowing the compound represented by the formula (4), which has been obtained by the step (v), to react with an enzyme, cells containing the enzyme, a preparation of the cells, or a culture solution obtained by culturing the cells, so as to produce an optically active compound represented by the formula (5).

[6] The method according to [4], wherein the step (vi) is a step (vi-2) of hydrolyzing the compound represented by the formula (4) obtained by the step (v) to produce a compound represented by the following formula (5a):

[Formula 9]

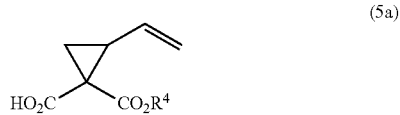

(5a)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted, and then subjecting the compound represented by the formula (5a) to optical resolution using an enzyme, cells containing the enzyme, a preparation of the cells, or a culture solution obtained by culturing the cells, or to optical resolution using an optically active basic compound or by chromatography, to produce an optically active compound represented by the formula (5).

[7] The method according to [4], wherein the step (vi) is a step (vi-3) of subjecting the compound represented by the formula (4) obtained by the step (v) to optical resolution using an enzyme, cells containing the enzyme, a preparation of the cells, or a culture solution obtained by culturing the cells, or to optical resolution by chromatography, to produce a compound represented by the following formula (4a):

[Formula 10]

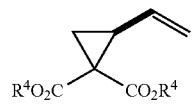

(4a)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted,
and then hydrolyzing the compound represented by the formula (4a), to produce an optically active compound represented by the formula (5).
[8] The method according to any one of [4] to [7], wherein the absolute stereochemistry of the compound represented by the formula (5) is (1S,2S).
[9] A method for producing a compound represented by the following formula (7):

[Formula 13]

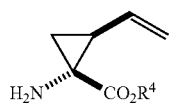

(7)

wherein $R^4$ represents an alkyl group containing 1 to 10 carbon atoms, an aralkyl group containing 7 to 20 carbon atoms, or an aryl group containing 6 to 12 carbon atoms, each of which may be optionally substituted,
or by the following formula (8):

[Formula 14]

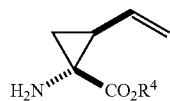

(8)

wherein $R^4$ represents an alkyl group containing 1 to 10 carbon atoms, an aralkyl group containing 7 to 20 carbon atoms, or an aryl group containing 6 to 12 carbon atoms, each of which may be optionally substituted; and HY represents an inorganic acid, sulfonic acid, or carboxylic acid,
wherein the method comprises:
a step (vi) of producing a compound represented by the following formula (5) by the method according to any one of [4] to [7]:

[Formula 11]

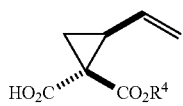

(5)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted;
a step (vii), in which (vii-1) the compound represented by the formula (5) obtained by the above step (vi) is allowed to react with a condensation agent or an acid halogenating agent to obtain a reaction intermediate, and the reaction intermediate is then allowed to react with a metal azide compound or a trialkylsilyl azide, or
(vii-2) the compound represented by the formula (5) obtained by the above step (vi) is allowed to react with a phosphoric acid ester-azide,
so as to obtain an acid azide, and the acid azide is then converted to an isocyanate, and the isocyanate is further allowed to react with an alcohol, thereby producing a compound represented by the following formula (6):

[Formula 12]

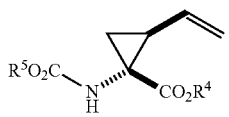

(6)

wherein $R^4$ and $R^5$ each independently represent an alkyl group containing 1 to 10 carbon atoms, an aralkyl group containing 7 to 20 carbon atoms, or an aryl group containing 6 to 12 carbon atoms, each of which may be optionally substituted; and
a step (viii) of allowing the compound represented by the above formula (6) obtained by the above step (vii) to react with an acid or a base, or subjecting the compound represented by the formula (6) to a catalytic hydrogenation reaction, so as to produce the compound represented by the formula (7) or the formula (8).
[10] The method according to [9], wherein, in the step (vii-1), the reaction intermediate is allowed to react with a metal azide compound or a trialkylsilyl azide in the presence of an acid.
[11] The method according to [9] or [10], wherein the absolute stereochemistry of the compound represented by the formula (5) is (1S,2S), and the absolute stereochemistry of each of the compounds represented by the formula (6), the formula (7) and the formula (8) is (1R,2S).
[12] A method for producing a compound represented by the following formula (7):

[Formula 16]

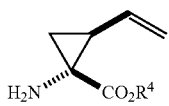

(7)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted, or by the following formula (8):

[Formula 17]

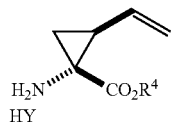

(8)

wherein $R^4$ represents an alkyl group containing 1 to 10 carbon atoms, an aralkyl group containing 7 to 20 carbon atoms, or an aryl group containing 6 to 12 carbon atoms, each of which may be optionally substituted; and HY represents an inorganic acid, sulfonic acid, or carboxylic acid,
wherein the method comprises:
a step (vi) of producing a compound represented by the following formula (5) by the method according to any one of [4] to [7]:

[Formula 15]

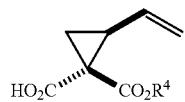

(5)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted; and
a step (ix), in which
(ix-1) the compound represented by the formula (5) obtained by the above step (vi) is allowed to react with a condensation agent or an acid halogenating agent to obtain a reaction intermediate, and the reaction intermediate is then allowed to react with a metal azide compound or a trialkylsilyl azide, or
(ix-2) the compound represented by the formula (5) obtained by the above step (vi) is allowed to react with a phosphoric acid ester-azide,
so as to obtain an acid azide, and the acid azide is then converted to an isocyanate, and the isocyanate is further allowed to react with water in the presence of an acid, thereby producing the compound represented by the formula (7) or the formula (8).
[13] The method according to [12], wherein, in the step (ix-1), the reaction intermediate is allowed to react with a metal azide compound or a trialkylsilyl azide in the presence of an acid.
[14] The method according to [12] or [13], wherein the absolute stereochemistry of the compound represented by the formula (5) is (1S,2S), and the absolute stereochemistry of each of the compounds represented by the formula (7) and the formula (8) is (1R,2S).
[15] A method for producing a compound represented by the following formula (7):

[Formula 19]

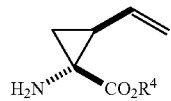

(7)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted, wherein the method comprises:
a step (x) of producing a compound represented by the following formula (8) by the method according to any one of [9] to [14]:

[Formula 18]

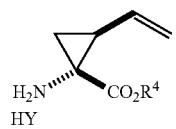

(8)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted; and HY represents an inorganic acid, sulfonic acid, or carboxylic acid; and
a step (xi) of allowing the compound represented by the formula (8) obtained by the above step (x) to react with a base.
[16] A method for producing a compound represented by the following formula (8):

[Formula 21]

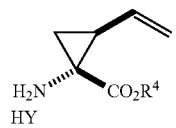

(8)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted; and HY represents an inorganic acid, sulfonic acid, or carboxylic acid,
wherein the method comprises:
a step (xii) of producing a compound represented by the following formula (7) by the method according to any one of [9] to [15]:

[Formula 20]

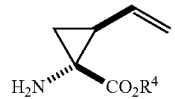

(7)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted; and
a step (xiii) of allowing the compound represented by the formula (7) obtained by the above step (xii) to react with an inorganic acid, sulfonic acid, or carboxylic acid.
[17] The method according to [16], wherein the step (xiii) is a step of allowing the compound represented by the formula (7) obtained by the above step (xii) to react with sulfuric acid in the presence of an organic solvent.

[18] The method according to any one of [9] to [17], which comprises a step of recrystallizing the compound represented by the formula (8).

Effects of Invention

According to the present invention, (1R,2S)/(1S,2R)-1-amino-1-alkoxycarbonyl-2-vinylcyclopropane, which is useful as a synthetic intermediate of therapeutic agents for hepatitis C, and a synthetic intermediate thereof, can be produced by an industrially applicable method. The production method of the present invention can be used in the production of therapeutic agents for hepatitis C and a synthetic intermediate thereof. The compound produced by the production method of the present invention can be used as a starting substance in the production of therapeutic agents for hepatitis C.

EMBODIMENTS FOR CARRYING OUT THE INVENTION

Hereinafter, the embodiments for carrying out the present invention will be described in detail.
(A) Production of Compound Represented by Formula (4)
According to the present invention, a compound represented by the following formula (4) can be produced:

[Formula 23]

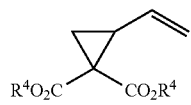

(4)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted, wherein
the method of the present invention comprises a step (i) of allowing a compound represented by the following formula (3):

[Formula 22]

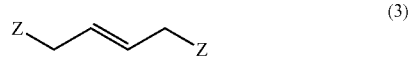

(3)

wherein Z represents a halogen atom or $OR^3$, wherein $R^3$ represents an arylsulfonyl group containing 6 to 12 carbon atoms, an alkylsulfonyl group containing 1 to 10 carbon atoms, or an aralkylsulfonyl group containing 7 to 20 carbon atoms, each of which may be optionally substituted,
to react with a malonic ester in the presence of an alkali metal alkoxide or alkali metal hydride so as to produce the compound represented by the formula (4),
wherein, in the step (i), the alkali metal alkoxide or alkali metal hydride is used in an amount of 1.5 equivalents or more with respect to 1 equivalent of the compound represented by the above formula (3), and the malonic ester is used in an amount of 1 equivalent or more with respect to 1 equivalent of the alkali metal alkoxide or alkali metal hydride.

A compound serving as a reaction substrate in the step (i) of the present invention, which is represented by the formula (3) in which Z represents a halogen atom, can be a commercially available product or can be easily produced by applying a known method, such as the method described in Glenn S. Skinner et al., J. Am. Chem. Soc. 1950, 70, 1648-1649.

A method of obtaining a compound serving as a reaction substrate in the step (i) of the present invention, which is represented by the formula (3) in which Z represents $OR^3$, will be described later.

The cyclopropane ring in the reaction product represented by the formula (4) in the step (i) of the present invention can be formed by nucleophilic addition of a malonic ester to the compound represented by the formula (3) in which Z represents a halogen atom or $OR^3$, and dissociation of Z.

In the reaction of forming such a cyclopropane ring, the compound represented by the formula (3) having a cis configuration generates 1,1-di-alkoxycarbonyl-3-cyclopentene as a by-product at a higher rate than the compound represented by the formula (3) having a trans configuration. Accordingly, in order to more efficiently obtain the compound represented by the formula (4), the compound represented by the formula (3) desirably has a trans configuration.

In the reaction of forming the cyclopropane ring in the step (i) of the present invention, a first asymmetric configuration is generated at position 2 of the cyclopropane ring. The produced compound represented by the formula (4) is a racemic form.

In the formula (3), halogen atoms represented by Z include fluorine, chlorine, bromine and iodine atoms. From the viewpoint of reaction selectivity, a bromine atom is preferable.

In the formula (3), examples of the arylsulfonyl group containing 6 to 12 carbon atoms, the alkylsulfonyl group containing 1 to 10 carbon atoms and the aralkylsulfonyl group containing 7 to 20 carbon atoms, each of which may be optionally substituted, which is represented by $R^3$, include a benzenesulfonyl group, a p-toluenesulfonyl group, a 1-naphthalenesulfonyl group, a 2-naphthalenesulfonyl group, a methanesulfonyl group, an ethanesulfonyl group, a propanesulfonyl group, a trifluoromethanesulfonyl group, and a benzylsulfonyl group.

$R^3$ is preferably an arylsulfonyl group containing 6 to 12 carbon atoms or an alkylsulfonyl group containing 1 to 10 carbon atoms, each of which may be optionally substituted. $R^3$ is more preferably an arylsulfonyl group containing 6 to 10 carbon atoms or an alkylsulfonyl group containing 1 to 8 carbon atoms, each of which may be optionally substituted. $R^3$ is further preferably an arylsulfonyl group containing 6 to 8 carbon atoms or alkylsulfonyl group containing 1 to 5 carbon atoms. Specifically, a methanesulfonyl group, a benzenesulfonyl group, and a p-toluenesulfonyl group are preferable. Of these, a p-toluenesulfonyl group is particularly preferable, since a crystal of a compound represented by a formula (3b), which will be described later, has high quality, and the recovery of the compound by crystallization can be carried out efficiently.

In the formula (4), an example of the alkyl group containing 1 to 10 carbon atoms which may be optionally substituted, which is represented by $R^4$, is a substituted or unsubstituted, linear, branched or cyclic alkyl group containing 1 to 10 carbon atoms. A substituted or unsubstituted, linear, branched or cyclic alkyl group containing 1 to 6 carbon atoms is more preferable. Among these groups, preferred examples include a methyl group, an ethyl group, an isopropyl group, a normal propyl group, a normal butyl group, an isobutyl group, a sec-butyl group, a tert-butyl group, a normal pentyl group, an isopentyl group, a tert-pentyl group, a neopentyl group, a normal hexyl group, a cyclopropyl group, a cyclobutyl group, a cyclopentyl group, and a cyclohexyl group. An alkyl group containing 1 to 4 carbon atoms is particularly preferable.

In the general formula (4), the aralkyl group containing 7 to 20 carbon atoms which may be optionally substituted, which is represented by $R^4$, is preferably a substituted or unsubstituted aralkyl group containing 7 to 12 carbon atoms. Among these groups, preferred examples include a benzyl group, a 4-methylbenzyl group, a 4-methoxybenzyl group, a 4-chlorobenzyl group, a 4-bromobenzyl group, a 2-phenylethyl group, a 1-phenylethyl group, and a 3-phenylpropyl group.

In the general formula (4), examples of the aryl group containing 6 to 12 carbon atoms which may be optionally substituted, which is represented by $R^4$, include a phenyl group, a 1-naphthyl group, a 2-naphthyl group, an o-methylphenyl group, a m-methylphenyl group, a p-methylphenyl group, an o-methoxyphenyl group, a m-methoxyphenyl group, a p-methoxyphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,3,5-trimethylphenyl group, a 2,3,6-trimethylphenyl group, a 2,4,6-trimethylphenyl group, an o-nitrophenyl group, a m-nitrophenyl group, and a p-nitrophenyl group.

$R^4$ is preferably a methyl group, an ethyl group, a tert-butyl group, or a benzyl group, and is more preferably an ethyl group.

In the step (i), the compound represented by the formula (3) is allowed to react with a malonic ester in the presence of an alkali metal alkoxide or alkali metal hydride. Examples of the alkali metal alkoxide that can be used herein include lithium ethoxide, lithium methoxide, lithium tert-butoxide, sodium ethoxide, sodium methoxide, sodium tert-butoxide, potassium ethoxide, potassium methoxide, and potassium tert-butoxide. Examples of the alkali metal hydride that can be used herein include lithium hydride, sodium hydride, and potassium hydride. However, the examples are not limited thereto.

In the step (i), the alkali metal alkoxide or alkali metal hydride is used in an amount of 1.5 equivalents or more with respect to 1 equivalent of the compound represented by the formula (3). In addition, the malonic ester is used in an amount of 1 equivalent or more with respect to 1 equivalent of the alkali metal alkoxide or alkali metal hydride. Using the alkali metal alkoxide or alkali metal hydride and the malonic ester in the aforementioned amounts, the remaining of raw materials and generation of by-products can be suppressed.

The amount of the alkali metal alkoxide or alkali metal hydride used is generally 1.5 equivalents or more, preferably 1.8 equivalents or more, and more preferably 2.0 equivalents or more, with respect to 1 equivalent of the compound represented by the formula (3). In addition, it is generally 3.0 equivalents or less, preferably 2.5 equivalents or less, and more preferably 2.2 equivalents or less, with respect to 1 equivalent of the compound represented by the formula (3).

Moreover, the amount of the malonic ester used is generally 1.5 equivalents or more, preferably 1.8 equivalents or more, and more preferably 2.0 equivalents or more, with respect to 1 equivalent of the compound represented by the formula (3). In addition, it is generally 3.0 equivalents or less, preferably 2.5 equivalents or less, and more preferably 2.2 equivalents or less, with respect to 1 equivalent of the compound represented by the formula (3).

The amount of the malonic ester used is generally 1.0 equivalent or more, with respect to 1 equivalent of the alkali metal alkoxide or alkali metal hydride. In addition, it is generally 2.0 equivalents or less, and preferably 1.5 equivalents or less. By adopting such amount ratios, the reaction selectivity in the step (i) is significantly improved.

The type of a reaction solvent is not particularly limited, as long as it does not inhibit the reaction. A plurality of solvents may be used in combination, at any given ratio. Examples of such a solvent include: alcohol solvents such as methanol, ethanol, normal propyl alcohol, isopropyl alcohol, and normal butanol; ketones such as acetone, 2-butanone, and methyl isobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; ethers such as diethyl ether, di-normal propyl ether, diisopropyl ether, di-normal butyl ether, methylisopropyl ether, methyl-tert-butyl ether, ethyl-tert-butyl ether, cyclopentylmethyl ether, tetrahydrofuran, dioxane, and 1,2-dimethoxyethane; amides such as N,N-dimethylformamide, N,N-dimethylacetamide, and N-methylpyrrolidone; halogenated hydrocarbons such as dichloromethane, chloroform, carbon tetrachloride, and 1,2-dichloroethane; and dimethyl sulfoxide. Among these substances, toluene, xylene, tetrahydrofuran, methanol, and ethanol are preferable; and toluene, ethanol, and a mixed solvent thereof are more preferable.

The method according to the present invention can be generally carried out at a temperature from −20° C. to 100° C. The temperature that is advantageous for the reaction is preferably from 0° C. to 80° C., and more preferably from 20° C. to 50° C. The reaction time is generally 1 to 40 hours, preferably 2 to 24 hours, and more preferably 2 to 8 hours.

In the method according to the present invention, after the compound represented by the formula (3) has been allowed to react with a malonic ester in the presence of an alkali metal alkoxide or alkali metal hydride, the malonic ester remains. By adding the compound represented by the formula (3) and an alkyl metal compound or an alkali metal hydride to the malonic ester remaining in the reaction solution at the above-mentioned amount ratio, the compound represented by the formula (4) can be further produced. This operation can be carried out repeatedly.

Furthermore, the compound represented by the formula (4) obtained, by the above step (i) is preferably purified before being subjected to the subsequent step.

The compound represented by the formula (4) can be purified by separating the remaining malonic ester from the compound represented by the formula (4).

The remaining malonic ester can be separated from the compound represented by the formula (4) by distillation, chromatography, or an operation of selectively hydrolyzing and extracting the malonic ester. Among others, the operation of selectively hydrolyzing and extracting the malonic ester is preferable in terms of high operability. Specifically, after completion of the reaction, a base, water, and a water-insoluble organic solvent are added to the reaction solution, so that the malonic ester is hydrolyzed, and thereafter, a water layer is removed by a liquid separation operation. By this method, it becomes possible to separate the remaining malonic ester more efficiently and in a shorter time than those by distillation or chromatography. The compound represented by the formula (4) can be obtained by an extraction operation using an organic solvent and the removal of the solvent by concentration.

After completion of the reaction, the operation of selectively hydrolyzing the malonic ester may be carried out after the separation of a mixture of the compound represented by the formula (4) and the malonic ester. Alternatively, the aforementioned operation may also be carried out continuously by adding a base and water to the reaction solution, without once removing the mixture of the compound represented by the formula (4) and the malonic ester.

In general, inorganic bases such as hydroxide, carbonate or bicarbonate of alkali metal are used as bases in the above-described hydrolysis. Specific examples include lithium hydroxide, sodium hydroxide, potassium hydroxide, potassium carbonate, and sodium carbonate. Among these compounds, lithium hydroxide, sodium hydroxide and potassium hydroxide are preferable; and sodium hydroxide is more preferable.

The amount of the base used is generally 0.5 equivalents to 20 equivalents, preferably 1 equivalent to 10 equivalents, and more preferably 1 equivalent to 3 equivalents, with respect to 1 equivalent of the remaining malonic ester. The reaction time is generally 5 minutes to 24 hours, preferably 10 minutes to 12 hours, and more preferably 30 minutes to 4 hours. The reaction temperature is generally from −20° C. to 100° C., preferably from −10° C. to 60° C., and more preferably from 0° C. to 40° C.

The type of an organic solvent to be added is not particularly limited, as long as it is able to separate from water. A plurality of organic solvents may be used in combination, at any given ratio. The type of a reaction solvent is not particularly limited, as long as it does not inhibit the reaction. A plurality of reaction solvents may be used in combination, at any given ratio. Examples of such a solvent include: aromatic hydrocarbons such as benzene, toluene, xylene, chlorobenzene, and trifluoromethylbenzene; ketones such as 2-butanone and methyl isobutyl ketone; aliphatic hydrocarbons such as n-pentane, n-hexane, n-heptane, and cyclohexane; ethers such as diethyl ether, di-normal propyl ether, diisopropyl ether, di-normal butyl ether, methylisopropyl ether, methyl-tert-butyl ether, ethyl-tert-butyl ether, cyclopentylmethyl ether, and 1,2-dimethoxyethane; and halogenated hydrocarbons such as dichloromethane, chloroform, carbon tetrachloride, and 1,2-dichloroethane. Among these substances, benzene, toluene, xylene, and the like are preferable.

The compound serving as a reaction substrate in the step (i), which is represented by the formula (3) in which Z represents $OR^3$, is identical to the compound represented by the formula (3a) that is a reaction product in the step (iv). This compound can be produced according to a publicly known method, such as the method described, for example, in Frederic Dolle et al., Bioorg. Med. Chem. 2006, 14, 1115-1125. Alternatively, this compound can be obtained by the following steps of the present invention:

a step (ii) of hydrolyzing, with an acid or a base, a compound represented by the following formula (1):

[Formula 24]

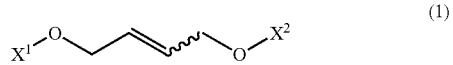
(1)

wherein $X^1$ represents a hydrogen atom or $R^1$, and $X^2$ represents a hydrogen atom or $R^2$, wherein $R^1$ and $R^2$ each independently represent an alkylcarbonyl group containing 2 to 11 carbon atoms, an aralkylcarbonyl group containing 8 to 21 carbon atoms or an arylcarbonyl group containing 7 to 13 carbon atoms, each of which may be optionally substituted, provided that $X^1$ and $X^2$ do not simultaneously represent hydrogen atoms, so as to produce a compound represented by the following formula (2):

[Formula 25]

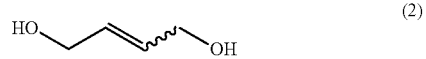
(2)

a step (iii) of allowing the compound represented by the formula (2), which has been obtained by the above step (ii), to react with a compound represented by $R^3X$ (wherein $R^3$ represents an arylsulfonyl group containing 6 to 12 carbon atoms, an alkylsulfonyl group containing 1 to 10 carbon atoms or an aralkylsulfonyl group containing 7 to 20 carbon atoms, each of which may be optionally substituted; and X represents a halogen atom), so as to produce a compound represented by the following formula (3b):

[Formula 26]

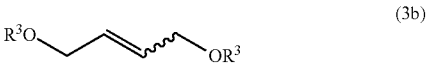
(3b)

wherein $R^3$ represents an arylsulfonyl group containing 6 to 12 carbon atoms, an alkylsulfonyl group containing 1 to 10 carbon atoms or an aralkylsulfonyl group containing 7 to 20 carbon atoms, each of which may be optionally substituted; and a step (iv) of crystallizing the compound represented by the formula (3b), which has been obtained by the above step (iii), so as to produce a compound represented by the following (3a):

[Formula 27]

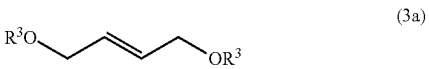
(3a)

wherein $R^3$ represents an arylsulfonyl group containing 6 to 12 carbon atoms, an alkylsulfonyl group containing 1 to 10 carbon atoms or an aralkylsulfonyl group containing 7 to 20 carbon atoms, each of which may be optionally substituted.

In the formula (1), $R^1$ and $R^2$ each independently represent an alkylcarbonyl group containing 2 to 11 carbon atoms, an aralkylcarbonyl group containing 8 to 21 carbon atoms or an arylcarbonyl group containing 7 to 13 carbon atoms, each of which may be optionally substituted. These groups are the same as carbonyl groups having an aryl group containing 6 to 12 carbon atoms, an alkyl group containing 1 to 10 carbon atoms, and an aralkyl group containing 7 to 20 carbon atoms, which are described above in the present specification. Examples of preferred $R^1$ and $R^2$ include an acetyl group, an ethylcarbonyl group, a normal propylcarbonyl group, an isopropylcarbonyl group, a normal butylcarbonyl group, an isobutylcarbonyl group, a sec-butylcarbonyl group, a tert-butylcarbonyl group, a normal pentylcarbonyl group, an isopentylcarbonyl group, a tert-pentylcarbonyl group, a neopentylcarbonyl group, a normal hexylcarbonyl group, a cyclopropylcarbonyl group, a cyclobutylcarbonyl group, a cyclopentylcarbonyl group, a cyclohexylcarbonyl group, a benzylcarbonyl group, a 2-phenylethylcarbonyl group, a 1-phenylethylcarbonyl group, a 3-phenylpropylcarbonyl group, a 4-methylbenzylcarbonyl group, a 4-methoxybenzylcarbonyl group, a 4-chlorobenzylcarbonyl group, a 4-bromobenzylcarbonyl group, a benzoyl group, a 4-methylphenylcarbonyl group, a 4-chlorophenylcarbonyl group, a 4-bromophenylcarbonyl group, a 4-methoxyphenylcarbonyl group, a 1-naphthylcarbonyl group, and a 2-naphthylcarbonyl group.

Among others, $R^1$ and $R^2$ each independently represent, preferably an alkylcarbonyl group containing 2 to 11 carbon atoms or an arylcarbonyl group containing 7 to 13 carbon atoms, optionally substituted, and represent more preferably an acetyl group, ethylcarbonyl group, tert-butylcarbonyl group or benzoyl group, and represents further preferably an acetyl group.

$R^3$ in the formulae (3b) and (3a) has the same definitions as those of $R^3$ in the formula (3).

The compound represented by the formula (1) in the step (ii) can be produced, for example, by the reaction of 2-buten-1,4-diol with acetic anhydride, or by the reaction of butadiene with acetic acid.

Preferred examples of the acid or base used in the hydrolysis of the compound represented by the formula (1) include: bases such as lithium hydroxide, sodium hydroxide, potassium hydroxide, lithium carbonate, sodium carbonate, potassium carbonate, lithium methoxide, lithium tert-butoxide, sodium ethoxide, sodium methoxide, sodium tert-butoxide, potassium ethoxide, potassium methoxide, and potassium tert-butoxide; and acids such as hydrochloric acid and sulfuric acid.

Preferred examples of $R^3X$ used in the step (iii) include methanesulfonic chloride, ethanesulfonic chloride, normal propanesulfonic chloride, isopropanesulfonic chloride, normal butanesulfonic chloride, trifluoromethanesulfonic chloride, phenylsulfonic chloride, p-toluenesulfonic chloride, p-ethylphenylsulfonic chloride, p-normal butylphenylsulfonic chloride, p-tertbutylphenylsulfonic chloride, p-methoxyphenylsulfonic chloride, p-trifluoromethylphenylsulfonic chloride, p-chlorophenylsulfonic chloride, p-bromophenylsulfonic chloride, p-iodophenylsulfonic chloride, p-cyanophenylsulfonic chloride, p-nitrophenylsulfonic chloride, and benzylsulfonic chloride.

The above-described hydrolysis of the compound represented by the formula (1) and the reaction of the compound represented by the above formula (2) with the compound represented by $R^3X$ can be carried out, for example, by mixing the compounds represented by the formula (1), a solvent that does not affect the reaction, a base, and a phase-transfer catalyst (e.g. tetra-n-butylammonium bromide, tetra-n-butylammonium chloride, benzyltriethylammonium chloride, benzyltriethylammonhen bromide, trioctylmethylammonium chloride, etc.), then stirring the obtained mixture at room temperature for a certain period of time, and then adding the compound represented by $R^3X$ to the reaction product, followed by performing a reaction at room temperature.

Examples of the solvent include: water; alcohols such as methanol, ethanol, normal propyl alcohol, isopropyl alcohol, and normal butanol; ketones such as acetone, 2-butanone, and methyl isobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-normal propyl ether, diisopropyl ether, di-normal butyl ether, methylisopropyl ether, methyl-tert-butyl ether, ethyl-tert-butyl ether, cyclopentylmethyl ether, tetrahydrofuran, dioxane, and 1,2-dimethoxyethane; amides such as N,N-dimethylformamide and N,N-dimethylacetamide; nitriles such as acetonitrile and propionitrile; and halogenated hydrocarbons such as dichloromethane, chloroform, carbon tetrachloride, and 1,2-dichloroethane. Preferred examples of the solvent include water; alcohols such as methanol, ethanol, normal propyl alcohol, and isopropyl alcohol; aromatic hydrocarbons such as benzene and toluene; ketones such as acetone, 2-butanone, and methyl isobutyl ketone; and amides such as N,N-dimethylformamide. More preferred examples of the solvent include water, ethanol, methyl isobutyl ketone, N,N-dimethylformamide, and a mixed solvent thereof. As bases, the same bases as those used in the above-described step (ii) can be used.

A trans form of the compound represented by the formula (3) can be obtained by crystallizing the compound represented by the formula (3). The crystallization method is not particularly limited. The compound represented by the formula (3) may be mixed with a solvent that does not affect crystallization, and the aforementioned compound may be then dissolved in the solvent by increasing the temperature. Thereafter, the mixture may be gradually cooled, for example, to ice chilled temperature, so as to precipitate a crystal. Then, the precipitated crystal may be collected by filtration. Examples of the solvent used in crystallization include aromatic hydrocarbon solvents, alcohol solvents, ether solvents, and a mixture of water and the aforementioned solvent. Preferred examples of the solvent include: aromatic hydrocarbon solvents such as toluene; alcohol solvents such as methanol, ethanol, normal propyl alcohol, isopropyl alcohol, and normal butanol; and ether solvents such as diethyl ether, diisopropyl ether, di-normal propyl ether, di-normal butyl ether, methylisopropyl ether, methyl-tert-butyl ether, ethyl-tert-butyl ether, cyclopentylmethyl ether, tetrahydrofuran, and dioxane.

(B) Production of Compound Represented by Formula (5)

According to the present invention, an optically active compound represented by the following formula (5):

[Formula 28]

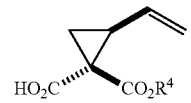

(5)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted, can be produced by the step (vi) wherein the compound represented by the formula (4), which has been produced by the method described in the above step (A), is subjected to hydrolysis, or to hydrolysis and optical resolution.

As a method of converting the compound represented by the formula (4) to the optically active compound represented by the formula (5), there can be applied a biochemical method (step (vi-1) of obtaining an optically active compound by a single step using an enzyme having ability to hydrolyze an ester group, cells containing the enzyme, a preparation of the cells, or a culture solution obtained by culturing the cells, or a method of performing hydrolysis and optical resolution by each different steps.

When hydrolysis and optical resolution are performed by each different steps, either a step (step (vi-2)) of hydrolyzing the compound represented by the formula (4), and then performing optical resolution on the obtained compound represented by the following formula (5a):

[Formula 29]

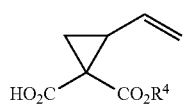

(5a)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted, or a step (step (vi-3)) of performing optical resolution on the compound represented by the formula (4), and then hydrolyzing an optically active compound represented by the following formula (4a):

[Formula 30]

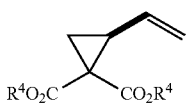

(4a)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted, may be selected.

$R^4$ found in the formula (5) in the above steps (vi-1) to (vi-3), the formula (5a) in the step (vi-2), and the formula (4a) in the step (vi-3), has the same definitions of those of $R^4$ defined in the previous formula (4).

In the hydrolysis performed by the biochemical method in the step (vi-1), an enzyme having ability to hydrolyze an ester group, cells containing the enzyme, a preparation of the cells, or a culture solution obtained by culturing the cells can be used. Such an enzyme, cells containing the enzyme, a preparation of the cells, or a culture solution obtained by culturing the cells, recognizes a stereo structure at position 2 on the cyclopropane ring in the compound represented by the formula (4) and acts preferentially on either one isomer, and at the same time, preferentially hydrolyzes only one of two ester groups at position 1 on the cyclopropane ring, so that it preferentially generates the optically active compound represented by the formula (5) having a configuration of a (1R,2R) form or a (1S,2S) form.

Alternatively, such an enzyme, cells containing the enzyme, a preparation of the cells, or a culture solution obtained by culturing the cells, recognizes a stereo structure at position 2 on the cyclopropane ring and acts on the two isomers. Then, regarding one of the two isomers, it preferentially hydrolyzes either one of two ester groups at position 1 on the cyclopropane ring, so that it preferentially generates the optically active compound represented by the formula (5) having a configuration of a (1R,2R) form or a (1S,2S) form. Regarding the other isomer, such an enzyme or the like hydrolyzes both of the two ester groups at position 1 on the cyclopropane ring.

The hydrolysis in the step (vi-2) and the step (vi-3) is carried out using a commercially available base such as lithium hydroxide, sodium hydroxide or potassium hydroxide, an acid such as hydrochloric acid or sulfuric acid, and an enzyme having ability to hydrolyze an ester group, cells containing the enzyme, a preparation of the cells, or a culture solution obtained by culturing the cells.

In the hydrolysis performed by the chemical method, only one of the two esters at position 1 on the cyclopropane ring is preferentially hydrolyzed, so that the compound represented by the formula (4) can be converted to the compound represented by the formula (5a), and as a result, a second asymmetric configuration is generated. In the stereo structure of the asymmetric configuration generated at position 1 on the cyclopropane ring as a result of the reaction, when the stereo structure at position 2 on the cyclopropane ring is S in the corresponding reaction substrate, S is predominant, whereas when the stereo structure at position 2 is R, R is predominant.

The optical resolution in the step (vi-2) and the step (vi-3) is carried out by a biochemical method using an enzyme, cells containing the enzyme, a preparation of the cells, or a culture solution obtained by culturing the cells, or by a chemical method using an optically active basic compound, or by a separation method such as chromatography.

In the optical resolution performed by the biochemical method in the step (vi-2), an enzyme, which has at least one ability selected from among ability to hydrolyze an ester group, transesterification ability, hydroxylation ability, ability to cleave a carbon-carbon bond, and ability to esterify, amidate, reduce or decarboxylate a carboxyl group, cells containing the aforementioned enzyme, a preparation of the cells, or a culture solution obtained by culturing the cells, can be used.

Moreover, in the optical resolution performed by the biochemical method in the step (vi-3), an enzyme having ability to hydrolyze and/or transesterify an ester group, or cells containing the aforementioned enzyme, a preparation of the cells or a culture solution obtained by culturing the cells, can be used.

The enzyme having the above-described ability can be used in the step (vi-1) to the step (vi-3). Specifically, an enzyme having ability to preferentially hydrolyze an ester group of either one isomer of, for example, the compound represented by the formula (4) or the compound represented by the formula (5a) can be used. Examples of the enzyme that can be used herein include pig liver-derived esterase, pig pancreas-derived lipase, carboxyl esterase NP, lipase E30000, lipase MY, *Rhizomucor miehei*-derived lipase, and *Bacillus subtilis*-derived para-nitrobenzyl esterase.

In particular, in the step (vi-1), carboxyl esterase NP and *Bacillus subtilis*-derived para-nitrobenzyl esterase can be preferably used. Using these enzymes, a hydrolysis and optical resolution can be carried out at high efficiency.

Moreover, in the step (vi-3), pig liver-derived esterase, pig pancreas-derived lipase, carboxyl esterase NP, lipase E30000, lipase MY, or *Rhizomucor miehei*-derived lipase can be preferably used. Using these enzymes, optical resolution can be carried out at high efficiency.

The enzyme used in the optical resolution is not limited to an isolated and purified enzyme. Cells containing such an enzyme, a preparation of the cells, a culture solution obtained by culturing the cells, and the like may also be used.

The method according to the present invention is generally carried out in an aqueous buffer. However, it can also be carried out in the presence of at least one organic solvent. When such a solvent is used, examples of the solvent used include glycerol, ethylene glycol, methanol, ethanol, 1-propanol, 2-propanol, dimethyl sulfoxide, dimethylformamide, n-hexane, n-heptane, ethyl acetate, isopropyl acetate, butyl acetate, benzene, toluene, xylene, acetone, 2-butanone, methyl isobutyl ketone, diethyl ether, di-normal propyl ether, diisopropyl ether, di-normal butyl ether, methylisopropyl ether, methyl-tert-butyl ether, ethyl-tert-butyl ether, cyclopentylmethyl ether, tetrahydrofuran, dioxane, 1,2-dimethoxyethane, acetonitrile, propionitrile, dichloromethane, chloroform, carbon tetrachloride, and 1,2-dichloroethane.

The method according to the present invention can be carried out generally at a temperature from 0° C. to 80° C. The temperature that is advantageous for the reaction depends on the thermostability of an enzyme. It is preferably from 20° C. to 50° C.

The reaction time that elapses before termination of the enzyme reaction is not particularly limited. It is generally about 1 to 120 hours, and preferably about 2 to 40 hours.

In the optical resolution performed by the chemical method, a racemic form of the compound represented by the formula (5a) is allowed to react with an optically active basic compound, so that it is converted to a mixture of two types of diastereomeric salts. Thereafter, the diastereomeric salts are divided by a physical method such as recrystallization, in which a difference in the crystallinity of the diastereomeric salts or a difference in the solubility in a solvent is utilized. The thus divided diastereomeric salts can be converted to a desired optically active form of the compound represented by the formula (5) by being treated with an acid.

Specific examples of a resolving agent used for converting the compound of the formula (5a) to diastereomeric salts include: optically active amines such as (S)-phenylethylamine, (R)-phenylethylamine, (S)-naphthylethylamine, and (R)-naphthylethylamine; amino acid esters such as (S)-phenyl glycine methyl ester, (R)-phenyl glycine methyl ester, (S)-proline methyl ester, and (R)-proline methyl ester; amino acid amides such as (S)-proline amide and (R)-proline amide; amino acid derivatives such as (S)-phenyl glycinol and (R)-phenyl glycinol; and natural alkaloids such as cinchonine, cinchonidine, brucine, and strychnine.

An example of the separation method involving chromatography is a method of subjecting the racemic form represented by the formula (4) or the formula (5a) to an optical isomer separation column (chiral column), so as to separate an optical isomer therefrom.

In the case of liquid chromatography for example, a mixture of optical isomers is added to a chiral column, such as Chiralcel Series manufactured by Daicel Corporation, Chiralpak Series manufactured by Daicel Corporation, or TCI Chiral Series manufactured by Tokyo Chemical Industry Co., Ltd., and thereafter, the mixture is developed using water, various types of organic solvents, and buffers (e.g. n-hexane, ethanol, methanol, isopropanol, acetonitrile, trifluoroacetic acid, diethylamine, etc.), singly or in the form of a mixed solution, so as to separate an optical isomer therefrom.

In the case of gas chromatography, a mixture of optical isomers is injected into a chiral column that is a cyclodextrin column, such as SUPELCO DEX Series or Astec CHIRALDEX Series manufactured by Sigma-Aldrich, and the mixture is then developed using inert gas such as nitrogen, helium or argon, so as to separate an optical isomer therefrom.

Specific examples of a chiral column used in liquid chromatography include Chiralcel OD-RH (4.6 mm×250 mm; particle diameter: 5 μm) manufactured by Daicel Corporation, Chiralcel OD-H (4.6 mm×250 mm; particle diameter: 5 μm) manufactured by Daicel Corporation, Chiralcel OJ-H (4.6 mm×250 mm; particle diameter: 5 μm) manufactured by Daicel Corporation, Chiralpak AD-H (4.6 mm×250 mm; particle diameter: 5 μm) manufactured by Daicel Corporation, Chiralpak AD-RH (4.6 mm×250 mm; particle diameter: 5 μm) manufactured by Daicel Corporation, Chiralpak IA (4.6 mm×250 mm; particle diameter: 5 μm) manufactured by Daicel Corporation, Chiralpak IB (4.6 mm×250 mm; particle diameter: 5 μm) manufactured by Daicel Corporation, Chiralpak IC (4.6 mm×250 mm; particle diameter: 5 μm) manufactured by Daicel Corporation, Chiralcel OB-H (4.6 mm×250 mm; particle diameter: 5 μm) manufactured by Daicel Corporation, TCI Chiral MB-S (4.6 mm×150 mm; particle diameter: 5 (m) manufactured by Tokyo Chemical Industry Co., Ltd., TCI Chiral CH—S (4.6 mm×150 mm; particle diameter: 5 (m) manufactured by Tokyo Chemical Industry Co., Ltd., and TCI Chiral BP-S (4.6 mm×150 mm; particle diameter: 5 (m) manufactured by Tokyo Chemical Industry Co., Ltd. In addition, an example of a chiral column used in gas chromatography is CHIRALDEX G-TA (30 m×0.25 mm; membrane thickness: 0.12 (m) manufactured by Sigma-Aldrich. The above-described optical resolution methods are only some specific examples of optical resolution. The optical resolution method is not limited thereto.

The racemic form of the compound represented by the formula (4), which has been obtained by the step (v) of the present invention, is subjected to any reaction in the step (vi-1) to the step (vi-3), so as to obtain a compound (5) whose absolute stereochemistry is represented by (1S,2S) and/or (1R,2R). In the present invention, the step (vi-1) is preferable from industrial and economical viewpoints.

(C) Production of Compounds Represented by Formulae (7) and (8)

According to the present invention, (vii) the compound represented by the formula (5), which has been produced by the method described in the above step (B) is subjected to the following step (vii-1) or step (vii-2):

(vii-1) the compound represented by the formula (5) is allowed to react with a condensation agent or an acid halogenating agent to obtain a reaction intermediate represented by the following formula (9):

[Formula 31]

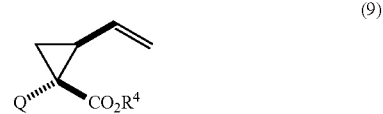

(9)

wherein Q represents —C(=O)OC(=O)OR$^6$ or —C(=O)A; R$^6$ has the same definitions as those of the above-described R$^4$; and A represents a halogen atom, and the reaction intermediate is then allowed to react with a metal azide compound or a trialkylsilyl azide, so as to obtain an acid azide, or (vii-2) the compound represented by the formula (5) is allowed to react with a phosphoric acid ester-azide, so as to obtain an acid azide.

Thereafter, the acid azide obtained by the above step (vii-1) or (vii-2) is converted to an isocyanate, and the isocyanate is further allowed to react with an alcohol, thereby producing a compound represented by the following formula (6):

[Formula 32]

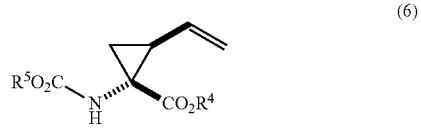

(6)

wherein $R^4$ and $R^5$ each independently represent an alkyl group containing 1 to 10 carbon atoms, an aralkyl group containing 7 to 20 carbon atoms or an aryl group containing 6 to 12 carbon atoms, each of which may be optionally substituted.

$R^4$ in the formula (6) in the above step (vii) has the same definitions as those of $R^4$ defined in the previous formula (4).

In the formula (6), the alkyl group containing 1 to 10 carbon atoms which may be optionally substituted, which is represented by $R^5$, is preferably a substituted or unsubstituted, linear, branched or cyclic alkyl group containing 1 to 10 carbon atoms. A substituted or unsubstituted, linear, branched or cyclic alkyl group containing 1 to 6 carbon atoms is more preferable. Of these alkyl groups, preferred examples include a methyl group, an ethyl group, an isopropyl group, a normal propyl group, a normal butyl group, an isobutyl group, a tert-butyl group, a normal hexyl group, and a cyclohexyl group.

In the formula (6), the aralkyl group containing 7 to 20 carbon atoms which may be optionally substituted, which is represented by $R^5$, is preferably a substituted or unsubstituted aralkyl group containing 7 to 12 carbon atoms. Of these aralkyl groups, preferred examples include a benzyl group, a 4-methylbenzyl group, a 4-methoxybenzyl group, a 4-chlorobenzyl group, and a 4-bromobenzyl group.

In the formula (6), preferred examples of the aryl group containing 6 to 12 carbon atoms which may be optionally substituted, which is represented by $R^5$, include a phenyl group, a 1-naphthyl group, a 2-naphthyl group, an o-methylphenyl group, a m-methylphenyl group, a p-methylphenyl group, an o-methoxyphenyl group, a m-methoxyphenyl group, a p-methoxyphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,3,5-trimethylphenyl group, a 2,3,6-trimethylphenyl group, a 2,4,6-trimethylphenyl group, an o-nitrophenyl group, a m-nitrophenyl group, and a p-nitrophenyl group.

$R^5$ is preferably a methyl group, an ethyl group, a tert-butyl group or a benzyl group, and is more preferably a tert-butyl group.

In the reaction in the step (vii), the carboxylic acid represented by the formula (5), in which the stereo structure at position 1 on the cyclopropane ring has an R or S form, is allowed to react with a condensation agent or an acid halogenating agent, so that it is converted to a mixed anhydride or an acid halide represented by the formula (9). A metal azide compound or a trialkylsilyl azide is allowed to act on the mixed anhydride or acid halide (step vii-1), or the carboxylic acid represented by the formula (5) is allowed to directly act on a phosphoric acid ester-azide (step vii-2), so as to generate an acid azide. A rearrangement reaction is promoted by heating the acid azide, and as a result, the acid azide is converted to an isocyanate. Thereafter, alcohol represented by $R^5OH$ is added to the generated isocyanate, so as to generate an aminocarboxylic acid ester of interest, which is represented by the formula (6).

In the step (vii), the reaction progresses, while the stereochemistry at position 1 on the cyclopropane ring is maintained. Thus, the compound of interest represented by the formula (6) can be obtained without a decrease in optical purity. In accordance with Cahn-Ingold-Prelog priority rule, when the compound of the formula (5) in which the stereo structure at position 1 on the cyclopropane ring is R is used, the stereochemistry at position 1 on the cyclopropane ring in the aminocarboxylic acid ester represented by the formula (6), which has been obtained by the step (vi), is named as S. When the compound S is used, the stereochemistry of the aminocarboxylic acid ester is named as R.

Examples of the condensation agent or acid halogenating agent that can be used in the step (vii-1) include methyl chloroformate, ethyl chloroformate, allyl chloroformate, isopropyl chloroformate, benzyl chloroformate, n-butyl chloroformate, isobutyl chloroformate, tert-butyl chloroformate, pivaloyl chloride, acetyl chloride, benzoyl chloride, thionyl chloride, thionyl bromide, phosphorus trichloride, phosphorus pentachloride, phosphorus oxytrichloride, phosphorous tribromide, phosphorous pentabromide, phosphorus oxytribromide, oxalyl chloride, oxalyl bromide, methanesulfonyl chloride, 4-toluenesulfonyl chloride, and trifluoromethanesulfonyl chloride. Among these compounds, methyl chloroformate, ethyl chloroformate, allyl chloroformate, isopropyl chloroformate, benzyl chloroformate, n-butyl chloroformate, isobutyl chloroformate, and tert-butyl chloroformate are preferably used.

In the step (vii-1) the condensation agent or acid halogenating agent can be used in a range generally from 0.7 to 10 equivalents, and preferably from 1 to 5 equivalents, with respect to 1 equivalent of the reaction substrate.

The reaction can be carried out generally at a temperature from −30° C. to 100° C. The temperature that is advantageous for the reaction is preferably from −10° C. to 50° C.

The reaction solvent is not particularly limited, as long as it does not inhibit the reaction. A plurality of solvents may be used in combination, at any given ratio. Examples of such a solvent include: ketones such as acetone, 2-butanone, and methyl isobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-normal propyl ether, diisopropyl ether, di-normal butyl ether, methylisopropyl ether, methyl-tert-butyl ether, ethyl-tert-butyl ether, cyclopentylmethyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and tertiary amines such as triethylamine, triisopropylamine, diisopropylethylamine, and N-methylmorpholine. Among these compounds, toluene, xylene, ethyl acetate, isopropyl acetate, tetrahydrofuran and triethylamine are preferable, and toluene is more preferable.

The reaction time is generally about 5 minutes to 20 hours, and preferably about 15 minutes to 3 hours.

In the azidation reaction in the step (vii), a metal azide compound, a trialkylsilyl azide, or a phosphoric acid ester-azide can be used as an azidating agent. Examples of the metal azide compound that can be used herein include sodium azide, potassium azide, and lithium azide. An example of the trialkylsilyl azide that can be used herein is trimethylsilyl azide. Examples of the phosphoric acid ester-azide that can be used herein include diphenylphosphoryl azide and diethyllphosphoryl azide.

In the above-described azidation reaction, the azidating agent can be used in a range generally from 0.7 to 10 equivalents, and preferably from 1 to 2 equivalents, with respect to 1 equivalent of the reaction substrate.

The reaction can be carried out generally at a temperature from −50° C. to 100° C. The temperature that is advantageous for the reaction is preferably from −10° C. to 30° C.

The reaction solvent is not particularly limited, as long as it does not inhibit the reaction. A plurality of solvents may be used in combination, at any given ratio. Examples of such a solvent include: water; ketones such as acetone, 2-butanone, and methyl isobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-normal propyl ether, diisopropyl ether, di-normal butyl ether, methylisopropyl ether, methyl-tert-butyl ether, ethyl-tert-butyl ether, cyclopentylmethyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and tertiary amines such as triethylamine, triisopropylamine, diisopropylethylamine, and N-methylmorpholine. Among these compounds, water, acetone, 2-butanone, methyl isobutyl ketone, toluene, xylene, ethyl acetate, isopropyl acetate, tetrahydrofuran and triethylamine are preferable, and water, acetone, toluene and a mixed solvent thereof are more preferable.

The reaction time is generally about 0.5 hours to 100 hours, and preferably about 1 hour to 20 hours.

In the step (vii), examples of the alcohol used to react with an isocyanate, after the acid azide has been converted to the isocyanate by performing a rearrangement reaction, include methanol, ethanol, propanol, isopropanol, tert-butyl alcohol, and benzyl alcohol.

In the rearrangement reaction in the step (vii), the alcohol can be used in a range generally from 0.9 to 20 equivalents, and preferably from 1 to 5 equivalents, with respect to 1 equivalent of the reaction substrate.

The reaction can be carried out generally at a temperature from 0° C. to 150° C. The temperature that is advantageous for the reaction is preferably from 40° C. to 100° C.

The reaction solvent is not particularly limited, as long as it does not inhibit the reaction. A plurality of solvents may be used in combination, at any given ratio. Examples of such a solvent include: ketones such as acetone, 2-butanone, and methyl isobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-normal propyl ether, diisopropyl ether, di-normal butyl ether, methylisopropyl ether, methyl-tert-butyl ether, ethyl-tert-butyl ether, cyclopentylmethyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and tertiary amines such as triethylamine, triisopropylamine, diisopropylethylamine, and N-methylmorpholine. Among these compounds, acetone, 2-butanone, methyl isobutyl ketone, toluene, xylene, ethyl acetate, isopropyl acetate, tetrahydrofuran and triethylamine are preferable, and acetone and toluene are more preferable.

The reaction time is generally about 1 hour to 40 hours, and preferably about 2 hours to 20 hours.

In the present invention,
(viii) the compound represented by the formula (6) obtained by the above step (vii) is allowed to react with an acid or a base, or is subjected to a catalytic hydrogenation reaction, so as to produce an amino acid ester represented by the following formula (7):

[Formula 31]

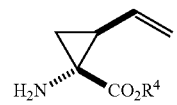

(7)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted,
or an amino acid ester salt represented by the following formula (8):

[Formula 34]

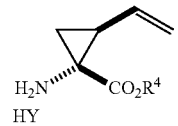

(8)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted; and HY represents an inorganic acid, sulfonic acid, or carboxylic acid.

$R^4$ in the formula (7) and the formula (8) in the above step (viii) has the same definitions as those of $R^4$ defined in the previous formula (4).

Specific examples of HY in the formula (8) in the above step (viii) include: inorganic acids such as HF, HCl, HBr, HI, ½$H_2SO_4$, $H_2SO_4$, ⅓$H_3PO_3$, ⅔$H_3PO_3$, and $H_3PO_3$; sulfonic acids such as methanesulfonic acid and p-toluenesulfonic acid; and carboxylic acids such as trifluoroacetic acid, tartaric acid, glutaric acid, citric acid, acetic acid, maleic acid, malic acid, and succinic acid. Preferred examples of HY include HCl, ½$H_2SO_4$, $H_2SO_4$, methanesulfonic acid, p-toluenesulfonic acid, and trifluoroacetic acid. Among these substances, HCl, ½$H_2SO_4$, $H_2SO_4$, and p-toluenesulfonic acid are particularly preferable because of a high deprotection reaction rate, high selectivity, good crystallinity, and good handlability.

With regard to the conversion of the carboxylic acid amide represented by the formula (6) to the amino acid ester represented by the formula (7) in the step (viii), the carboxylic acid amide can be converted to the amino acid ester represented by the formula (7) by a reaction of removing a protecting group from an amino group, or the carboxylic acid amide can be converted to the salt represented by the formula (8), followed by treating it with a base or the like, so as to obtain the amino acid ester represented by the formula (7).

Moreover, the reaction of converting the aminocarboxylic acid ester represented by the formula (6) to the amino acid ester salt represented by the formula (8) can be carried out by converting the aminocarboxylic acid ester to the amino acid ester represented by the formula (7) and then treating it with the corresponding acid to obtain the salt represented by the formula (8). Otherwise, the reaction of removing a protecting group from an amino group and the conversion to the salts can be carried out simultaneously.

Both the amino acid ester represented by the formula (7) and the amino acid ester salt represented by the formula (8) can be obtained by a reaction with an acid or a base, or by catalytic hydrogenation. In the case of obtaining the amino acid ester represented by the formula (7), it is preferable that the compound of formula (6) be subjected to a reaction with a base, catalytic hydrogenation, or a treatment with an acid or a solution containing such an acid, and be then treated with a base. In the case of obtaining the amino acid ester salt represented by the formula (8), it is preferable that the compound of formula (6) be subjected to a reaction with an acid, a reaction with a base, or catalytic hydrogenation, and be then treated with HY or a solution containing such HY.

Examples of the acid used in the reaction in the step (viii) include hydrogen fluoride, hydrochloric acid, hydrogen bromide, hydrogen iodide, sulfuric acid, phosphoric acid, acetic acid, and trifluoroacetic acid. Among these acids, hydrochloric acid and sulfuric acid are preferable. Examples of the base used herein include lithium hydroxide, sodium hydroxide, potassium hydroxide, sodium methoxide, sodium ethoxide, sodium t-butoxide, potassium ethoxide, potassium methoxide, potassium t-butoxide, sodium carbonate, lithium carbonate, and potassium carbonate. Among these compounds, sodium hydroxide and potassium hydroxide are more preferable.

Examples of a catalyst that is used in deprotection of an amino group by catalytic hydrogenation include palladium, ruthenium, platinum, an activated carbon mixture thereof, and a complex thereof. Among these catalysts, palladium carbon is preferably used.

In the reaction in the step (viii), the acid can be used in a range generally from 0.7 to 100 equivalents, and preferably from 1 to 5 equivalents, with respect to 1 equivalent of the reaction substrate. The base can be used in a range generally from 0.5 to 100 equivalents, and preferably from 0.5 to 5 equivalents, with respect to 1 equivalent of the reaction substrate.

The reaction can be carried out generally at a temperature from −20° C. to 150° C. The temperature that is advantageous for the reaction is preferably from 0° C. to 100° C., and more preferably from 10° C. to 80° C.

The reaction solvent is not particularly limited, as long as it does not inhibit the reaction. A plurality of solvents may be used in combination, at any given ratio. Examples of such a solvent include: water; alcohols such as methanol, ethanol, normal propyl alcohol, isopropyl alcohol, and normal butanol; ketones such as acetone, 2-butanone, and methyl isobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-normal propyl ether, diisopropyl ether, di-normal butyl ether, methylisopropyl ether, methyl-tert-butyl ether, ethyl-tert-butyl ether, cyclopentylmethyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and dimethyl sulfoxide. Among these compounds, ethanol, ethyl acetate, and dioxane are preferable.

The reaction time is generally about 5 minutes to 10 hours, and preferably about 0.5 hours to 2 hours.

Moreover, in the present invention, the compound represented by the formula (5), which has been produced by the method described in (B) above, (ix-1) is allowed to react with a condensation agent or an acid halogenating agent to obtain the reaction intermediate represented by the formula (9), and the obtained reaction intermediate is then allowed to react with a metal azide compound or a trialkylsilyl azide, so as to generate an acid azide, or (ix-2) is allowed to react with a phosphoric acid ester-azide, so as to generate an acid azide.

The acid azide obtained in the above (ix-1) or (ix-2) is converted to an isocyanate, and the isocyanate is allowed to further react with water in the presence of an acid (e.g. hydrochloric acid, a p-toluenesulfonic acid monohydrate, methanesulfonic acid, trifluoromethanesulfonic acid, sulfuric acid, phosphoric acid, hydrogen bromide, hydrogen fluoride, hydrogen iodide, etc.), so that the amino acid ester represented by the above formula (7) or the amino acid ester salt represented by the above formula (8) can be produced by a single step, without the mediation of production of the compound represented by the formula (6) (step (ix)).

In the reaction in the step (ix), the acid can be used in a range generally from 0.5 to 100 equivalents, and preferably from 1 to 5 equivalents, with respect to 1 equivalent of the reaction substrate.

The water can be used in a range generally from 0.7 to 300 equivalents, and preferably from 1 to 20 equivalents, with respect to 1 equivalent of the reaction substrate.

The reaction can be carried out generally at a temperature from 0° C. to 200° C. The temperature that is advantageous for the reaction is preferably from 15° C. to 100° C.

The reaction solvent is not particularly limited, as long as it does not inhibit the reaction. A plurality of solvents may be used in combination, at any given ratio. Examples of such a solvent include: ketones such as acetone, 2-butanone, and methyl isobutyl ketone; aromatic hydrocarbons such as benzene, toluene, xylene, chlorobenzene, and trifluoromethylbenzene; aliphatic hydrocarbons such as n-pentane, n-hexane, n-heptane, and cyclohexane; esters such as methyl acetate, ethyl acetate, and isopropyl acetate; ethers such as diethyl ether, di-normal propyl ether, diisopropyl ether, di-normal butyl ether, methylisopropyl ether, methyl-tert-butyl ether, ethyl-tert-butyl ether, cyclopentylmethyl ether, tetrahydrofuran, dioxane, and 1,2-dimethoxyethane; amides such as N,N-dimethylformamide and N,N-dimethylacetamide; nitriles such as acetonitrile and propionitrile; halogenated hydrocarbons such as dichloromethane, chloroform, carbon tetrachloride, and 1,2-dichloroethane; and dimethyl sulfoxide. Among these compounds, acetone, toluene, ethyl acetate, tetrahydrofuran, dioxane, and a mixed solvent thereof are preferable.

The reaction time is generally about 0.5 hours to 40 hours, and preferably about 1 hour to 15 hours.

As an acid used in the reaction in the step (ix), a p-toluenesulfonic acid monohydrate is particularly preferable. In the reaction in the step (ix), an organic solvent is preferably used to dissolve the compound represented by the formula (5), as well as water added as a reaction reagent. Since such a p-toluenesulfonic acid monohydrate is easily dissolved in such an organic solvent, when compared with inorganic acids such as hydrochloric acid or sulfuric acid, the reaction rapidly progresses. Moreover, since such a p-toluenesulfonic acid monohydrate contains 1 equivalent of water with respect to the acid, it enables easy incorporation of water into an organic solvent, when compared with other acids dissolved in an organic solvent, such as acetic acid, methanesulfonic acid or trifluoroacetic acid, and thus, it makes the control of water content easy. Using a solvent that dissolves such a p-toluenesulfonic acid monohydrate, the reaction system becomes homogeneous, and as a result, the compound represented by the formula (7) or the formula (8) can be obtained more selectively.

In the step (vii) or the step (ix), when the compound represented by the formula (5) is allowed to react with a condensation agent or an acid halogenating agent and is then allowed to react with a metal azide compound, an acid is preferably allowed to be present. As such an acid, hydrochloric acid, hydrobromic acid, sulfuric acid or the like can be used. The use of hydrochloric acid is particularly preferable. The reaction rate can be improved by adding hydrochloric acid, and generation of the compound of the formula (5) as a by-product can be suppressed. The concentration of the hydrochloric acid used is not particularly limited. It is 0.1 to 2 equivalents, and preferably 0.5 to 1 equivalent, with respect to the concentration of the azidating agent.

According to the present invention,
(x) the compound represented by the formula (8) is produced by the above-described step (viii) or step (ix), and
(xi) the obtained compound represented by the formula (8) is allowed to react with a base, so as to produce an amino acid ester represented by the following formula (7):

[Formula 35]

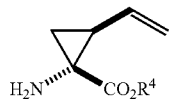

(7)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted.

Examples of the base used in the step (xi) include lithium hydroxide, sodium hydroxide, potassium hydroxide, sodium carbonate, lithium carbonate, potassium carbonate, sodium bicarbonate, and potassium bicarbonate. Among these compounds, sodium hydroxide, potassium hydroxide, sodium bicarbonate, and potassium bicarbonate are more preferable.

The base can be used in a range generally from 0.5 to 100 equivalents, and preferably from 0.5 to 5 equivalents, with respect to 1 equivalent of the reaction substrate. The reaction temperature can be in a range generally from −30° C. to 150° C., and preferably from −5° C. to 35° C. The reaction time is generally 0 minute to 10 hours, and preferably 5 minutes to 30 minutes.

The reaction solvent is not particularly limited, as long as it does not inhibit the reaction. A plurality of solvents may be used in combination, at any given ratio. Examples of such a solvent include water, alcohols such as methanol, ethanol, normal propyl alcohol, isopropyl alcohol and normal butanol, acetone, 2-butanone, methyl isobutyl ketone, benzene, toluene, xylene, chlorobenzene, trifluoromethylbenzene, n-pentane, n-hexane, n-heptane, cyclohexane, methyl acetate, ethyl acetate, isopropyl acetate, diethyl ether, di-normal propyl ether, diisopropyl ether, di-normal butyl ether, methylisopropyl ether, methyl-t-butyl ether, ethyl-t-butyl ether, cyclopentylmethyl ether, tetrahydrofuran, dioxane, 1,2-dimethoxyethane, N,N-dimethylformamide, N,N-dimethylacetamide, N-methylpyrrolidone, acetonitrile, propionitrile, dichloromethane, chloroform, carbon tetrachloride, 1,2-dichloroethane, and dimethyl sulfoxide. Among these compounds, water, toluene, di-normal propyl ether, diisopropyl ether, di-normal butyl ether, methylisopropyl ether, methyl-t-butyl ether, ethyl-t-butyl ether, cyclopentylmethyl ether, methyl acetate, ethyl acetate and isopropyl acetate are preferable, and water, methyl-t-butyl ether, toluene, ethyl acetate and a mixed solvent thereof are more preferable.

According to the present invention,
(xii) the compound represented by the formula (7) is produced by the above-described step (viii) or step (ix), and
(xiii) the obtained compound represented by the formula (7) is allowed to react with HY, so as to produce an amino acid ester salt represented by the following formula (8):

[Formula 36]

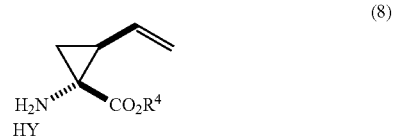

(8)

wherein $R^4$ represents an alkyl group containing 1 to 10 carbon atoms, an aralkyl group containing 7 to 20 carbon atoms or aryl group containing 6 to 12 carbon atoms, each of which may be optionally substituted; and HY represents an inorganic acid, sulfonic acid, or carboxylic acid.

Specific examples of the HY used in the step (xiii) include: inorganic acids such as HF, HCl, HBr, HI, ½H$_2$SO$_4$, H$_2$SO$_4$, ⅓H$_3$PO$_3$, ⅔H$_3$PO$_3$, and H$_3$PO$_3$; sulfonic acids such as methanesulfonic acid and p-toluenesulfonic acid; and carboxylic acids such as trifluoroacetic acid, tartaric acid, glutaric acid, citric acid, acetic acid, maleic acid, malic acid, and succinic acid. Preferred examples of HY include HCl, ½H$_2$SO$_4$, H$_2$SO$_4$, methanesulfonic acid, p-toluenesulfonic acid, and trifluoroacetic acid. Among these substances, HCl, ½H$_2$SO$_4$, H$_2$SO$_4$, and p-toluenesulfonic acid are particularly preferable because of a high deprotection reaction rate, high selectivity, good crystallinity, and good handlability.

The acid can be used in a range generally from 0.3 to 100 equivalents, and preferably from 0.5 to 1 equivalent, with respect to 1 equivalent of the reaction substrate. The reaction can be carried in a temperature range generally from −50° C. to 150° C., and preferably from −5° C. to 50° C. The reaction time is generally 0 minute to 10 hours, and preferably 0 minute to 1 hour.

The reaction solvent is not particularly limited, as long as it does not inhibit the reaction. A plurality of solvents may be used in combination, at any given ratio. Examples of such a solvent include water, alcohols such as methanol, ethanol, normal propyl alcohol, isopropyl alcohol, normal butanol and tert-butanol, acetone, 2-butanone, methyl isobutyl ketone, benzene, toluene, xylene, chlorobenzene, trifluoromethylbenzene, n-pentane, n-hexane, n-heptane, cyclohexane, methyl acetate, ethyl acetate, isopropyl acetate, diethyl ether, di-normal propyl ether, diisopropyl ether, di-normal butyl ether, methylisopropyl ether, methyl-t-butyl ether, ethyl-t-butyl ether, cyclopentylmethyl ether, tetrahydrofuran, dioxane, 1,2-dimethoxyethane, N,N-dimethylformamide, N,N-dimethylacetamide, N-methylpyrrolidone, acetonitrile, propionitrile, dichloromethane, chloroform, carbon tetrachloride, 1,2-dichloroethane, and dimethyl sulfoxide. Among these compounds, ethanol, ethyl acetate, isopropyl acetate, methyl-t-butyl ether and toluene are preferable, and ethanol, ethyl acetate, toluene and a mixed solvent thereof are more preferable.

In particular, when sulfuric acid is used as HY in the step (xiii), an organic solvent is preferably used as a reaction solvent. Since the compound represented by the formula (8), in which HY is ½H$_2$SO$_4$, has low solubility in an organic solvent, the compound of the formula (8), in which HY is ½H$_2$SO$_4$, can be efficiently isolated by crystallization.

As an organic solvent used herein, ethyl acetate or a mixed solvent of toluene and alcohol is preferable. Examples of the alcohol used herein include methanol, ethanol, normal propyl alcohol, isopropyl alcohol, normal butanol, and tert-butanol. Among these alcohols, methanol and ethanol are preferable, and ethanol is more preferable. Of these, ethyl acetate is most preferable.

Since ethyl acetate or a mixed solvent of toluene and alcohol easily dissolves sulfuric acid, generation of the compound represented by the formula (8), in which HY is ½H$_2$SO$_4$, progresses rapidly. In addition, the compound represented by the formula (8) in which HY is ½H$_2$SO$_4$, which has been generated in such a solvent, has good crystallinity, and thus, it can be efficiently collected by crystallization.

In the present invention, a step of recrystallizing the compound of the formula (8), in which HY is p-toluenesulfonic acid, is included in any one of the above-described steps, so that the optical purity of the compound represented by the formula (7) or the formula (8) can be improved.

The compound represented by the formula (8) in which HY is p-toluenesulfonic acid, which has been obtained by recrystallization, is subjected to the step (xi), so as to synthesize the compound represented by the formula (7).

Moreover, the compound represented by the formula (7) obtained by any one of the above-described steps is subjected to the step (xiii), so that the optical purity of the compound represented by the formula (8), in which HY is a substance other than p-toluenesulfonic acid, can also be improved.

The recrystallization method is not particularly limited. The compound represented by the formula (8), in which HY is p-toluenesulfonic acid, may be mixed with a solvent that does not affect crystallization, and it may be then dissolved therein by heating. Then, the mixture may be gradually cooled, so that a crystal can be precipitated. Thereafter, the precipitated crystal may be collected by filtration. Examples of the solvent used in the recrystallization include benzene, toluene, xylene, methyl acetate, ethyl acetate, and isopropyl acetate. Among these solvents, toluene and ethyl acetate are preferable.

The temperature applied to the dissolution by heating is generally from 20° C. to 150° C., and preferably from 40° C. to 70° C. The cooling temperature is generally from −50° C. to 80° C., and preferably from −10° C. to 25° C.

The compound represented by the formula (5) whose absolute stereochemistry is (1S,2S), which has been obtained by the step (vi) of the present invention, is subjected to the reaction in the step (viii) or the step (ix), so as to obtain the compounds represented by the formula (6), formula (7) and formula (8) whose absolute stereochemistry is (1R,2S). These compounds can be utilized as intermediates useful for the synthesis of various types of HCV NS3 protease inhibitors and the like, which are currently under development as therapeutic agents for hepatitis C.

Likewise, the compound represented by the formula (5) whose absolute stereochemistry is (1R,2R), which has been obtained by the step (vi) of the present invention, is subjected to the reaction in the step (viii) or the step (ix), so as to obtain the compounds represented by the formula (6), formula (7) and formula (8) whose absolute stereochemistry is (1S,2R).

EXAMPLES

Hereinafter, the present invention will be described more in detail in the following examples. However, these examples are not intended to limit the scope of the present invention.

Example 1

Production of 1,4-di-4-toluenesulfonyloxy-2-butene 10.0 g (58.1 mmol) of 1,4-diacetoxy-2-butene (trans/cis=85/15), 100 mL of toluene, and 50 mL of a 50% sodium hydroxide aqueous solution were added into a four-necked flask (300 mL), and thereafter, 0.936 g (2.90 mmol) of tetra-n-butylammonium bromide was added thereto as a phase-transfer catalyst. The obtained mixture was stirred at room temperature for 1 hour, and 27.7 g (145 mmol) of 4-toluenesulfonyl chloride was then added to the reaction solution. The obtained mixture was stirred at room temperature for 2.5 hours, and 100 mL of water and 50 mL of toluene were then added to the reaction solution to facilitate liquid separation. The mixture was stirred, and an organic layer was then separated. The organic layer was washed with 100 mL of water three times, and the resultant was then filtrated, while washing the residue with toluene. The obtained filtrate was concentrated at 45° C. under reduced pressure, so as to obtain 24.8 g of 1,4-di-4-toluenesulfonyloxy-2-butene in the form of a crude product of a light yellow solid (yield: 108%).

Example 2

Production of trans-1,4-di-4-toluenesulfonyloxy-2-butene 24.7 g of the crude product of 1,4-di-4-toluenesulfonyloxy-2-butene, which had been obtained in Example 1, and 49 mL of toluene, were added into a 200-mL flask, and the crude product was completely dissolved in the toluene at 60° C. Thereafter, the obtained solution was gradually cooled to 0° C., and it was then stirred for 1 hour. Thereafter, the precipitated crystal was collected by filtration. The obtained crystal was washed with 10 mL of cold toluene, and it was then dried at room temperature, so as to obtain 13.6 g of trans-1,4-di-4-toluenesulfonyloxy-2-butene in the form of a colorless crystal (yield: 55%, trans/cis=100/0). As a result of NMR analysis, the colorless crystal was confirmed to be trans-1,4-di-4-toluenesulfonyloxy-2-butene.

1H-NMR (400 MHz, CDCl$_3$) δ2.46 (6H, s), 4.47 (2H, d, J=1.5 Hz), 4.48 (2H, d, J=1.2 Hz), 5.74 (2H, ddd, J=1.2, 2.8, 4.3 Hz), 7.35 (4H, d, J=8.1 Hz), 7.77 (4H, dd, J=1.8, 8.4 Hz).

Example 3

Production of trans-1,4-di-4-toluenesulfonyloxy-2-butene 4.47 g of a crude product of 1,4-di-4-toluenesulfonyloxy-2-butene, which had been obtained in the same manner as that of Example 1, and 22 mL of ethanol, were added into a 50-mL flask, and the crude product was completely dissolved in the ethanol at 70° C. Thereafter, the obtained solution was gradually cooled to 0° C., and it was then stirred for 1 hour. Thereafter, the precipitated crystal was collected by filtration. The obtained crystal was washed with 4 mL of cold ethanol, and it was then dried at room temperature, so as to obtain 1.88 g of trans-1,4-di-4-toluenesulfonyloxy-2-butene in the form of a colorless crystal (yield: 42%, trans/cis=100/0). As a result of NMR analysis, the colorless crystal was confirmed to be trans-1,4-di-4-toluenesulfonyloxy-2-butene.

Example 4

Production of 1,4-di-4-toluenesulfonyloxy-2-butene 30.0 g (174 mmol) of 1,4-diacetoxy-2-butene (trans/cis=85/15), 300 mL of toluene, and 150 mL of a 50% sodium hydroxide aqueous solution were added into a four-necked flask (1 L), and thereafter, 2.81 g (8.71 mmol) of tetra-n-butylammonium bromide was then added thereto as a phase-transfer catalyst. The obtained mixture was stirred at room temperature for 1 hour, and 66.4 g (348 mmol) of 4-toluenesulfonyl chloride was then added to the reaction solution. The obtained mixture was stirred at room temperature for 6 hours, and 300 mL of water was then added to the reaction solution to facilitate liquid separation. The mixture was stirred, and an organic layer was then separated. A water layer was re-extracted with 150 mL of toluene, and organic layers were then gathered. The gathered organic layer was washed with 150 mL of water three times, and the resultant was filtrated, while washing the residue with toluene. The obtained filtrate was concentrated at 45° C. under reduced pressure. Thereafter, 60 mL of toluene was added to the residue, and the residue was completely dissolved therein at 60° C. Thereafter, the obtained solution was gradually cooled to 0° C., and it was then stirred for 1 hour. The precipitated crystal was collected by filtration. The obtained crystal was washed with 30 mL of cold toluene, and it was then dried at room temperature, so as to obtain 31.2 g of trans-1,4-di-4-toluenesulfonyloxy-2-butene in the form of a colorless crystal (yield: 45%, trans/cis=100/0). As a result of NMR analysis, the colorless crystal was confirmed to be trans-1,4-di-4-toluenesulfonyloxy-2-butene.

Example 5

Production of 1,4-di-4-toluenesulfonyloxy-2-butene 30.0 g (174 mmol) of 1,4-diacetoxy-2-butene (trans/cis=85/15), 150 mL of toluene, and 300 mL of a 50% sodium hydroxide aqueous solution were added into a four-necked flask (1 L), and thereafter, 2.81 g (8.71 mmol) of tetra-n-butylammonium bromide was added thereto as a phase-transfer catalyst. The obtained mixture was stirred at room temperature for 1 hour, and 79.7 g (418 mmol) of 4-toluenesulfonyl chloride was then added to the reaction solution. The obtained mixture was stirred at room temperature for 5 hours, and 480 mL of water and 150 mL of toluene were then added to the reaction solution to facilitate liquid separation. The mixture was stirred, and an organic layer was then separated. A water layer was re-extracted with 150 mL of toluene, and organic layers were then gathered. The gathered organic layer was washed with 120 mL of water three times, and the resultant was filtrated, while washing the residue with toluene. The obtained filtrate was concentrated at 45° C. under reduced pressure. Thereafter, 60 mL of toluene was added to the residue, and the residue was completely dissolved therein at 60° C. Thereafter, the obtained solution was gradually cooled to 0° C., and it was then stirred for 1 hour. The precipitated crystal was collected by filtration. The obtained crystal was washed with 30 mL of cold toluene, and it was then dried at room temperature, so as to obtain 35.4 g of trans-1,4-di-4-toluenesulfonyloxy-2-butene in the form of a colorless crystal (yield: 51%, trans/cis=100/0). As a result of NMR analysis, the colorless crystal was confirmed to be trans-1,4-di-4-toluenesulfonyloxy-2-butene.

Example 6

Production of 1,1-di-ethoxycarbonyl-2-vinylcyclopropane 0.89 g (5.55 mmol) of diethyl malonate and 10 mL of toluene were added into a three-necked flask (50 mL), and 2.08 mL (5.30 mmol) of a 20% sodium ethoxide ethanol solution was then added thereto as a base. The obtained mixture was stirred at room temperature for 0.5 hours, and thereafter, 1.00 g (2.52 mmol) of trans-1,4-di-4-toluenesulfonyloxy-2-butene, which had been obtained in the same manner as that of Example 4, was added to the reaction solution. The obtained mixture was stirred at room temperature for 5 hours, and 10 mL of water was then added to the reaction solution. The mixture was stirred, and an organic layer was then separated. The organic layer was washed with 10 mL of water twice, and with 10 mL of brine once. The resultant was filtrated, while washing the residue with toluene. The obtained filtrate was concentrated at 45° C. under reduced pressure, so as to obtain a crude product of a light yellow oily substance.

This crude product, 20 mL of toluene, and 5 mL of a 25% sodium hydroxide aqueous solution were added into a three-necked flask (50 mL), and thereafter, 40.7 mg (0.126 mmol) of tetra-n-butylammonium bromide was added thereto as a phase-transfer catalyst. The obtained mixture was stirred at room temperature for 3 hours, and an organic layer was then separated. The organic layer was washed with 5 mL of water twice, and with 5 mL of brine once. The resultant was filtrated, while washing the residue with toluene. The obtained filtrate was concentrated at 45° C. under reduced pressure, so as to obtain 518 mg of 1,1-di-ethoxycarbonyl-2-vinylcyclopropane in the form of a crude product of a light yellow oily substance. This crude product contained 496 mg of 1,1-di-ethoxycarbonyl-2-vinylcyclopropane (yield: 93%).

$^1$H-NMR (400 MHz, CDCl$_3$) δ1.27 (3H, t, J=7.2 Hz), 1.27 (3H, t, J=7.2 Hz), 1.55 (1H, dd, J=4.8, 8.8 Hz), 1.69 (1H, dd, J=4.8, 7.6 Hz), 2.58 (1H, ddd, J=7.6, 8.3, 8.8 Hz), 4.12-4.28 (4H, m), 5.14 (1H, ddd, J=0.5, 1.8, 10.1 Hz), 5.30 (1H, ddd, J=0.5, 1.5, 16.9 Hz) 5.44 (1H, ddd, J=8.3, 10.1, 16.9 Hz).

Example 7

Production of 1,1-di-ethoxycarbonyl-2-vinylcyclopropane 31.8 g (198 mmol) of diethyl malonate and 358 mL of toluene were added into a three-necked flask (1 L), and thereafter, 74.3 mL (190 mmol) of a 20% sodium ethoxide ethanol solution was then added thereto as a base. The obtained mixture was stirred at room temperature for 0.5 hours, and 35.8 g (90.3 mmol) of trans-1,4-di-4-toluenesulfonyloxy-2-butene, which had been obtained in the same manner as that of Example 4, was added to the reaction solution. The obtained mixture was stirred at room temperature for 23 hours, and 217 mL of a 1 M sodium hydroxide aqueous solution was then added to the reaction solution. The mixture was stirred for 1 hour, and an organic layer was then separated. A water layer was re-extracted with 180 mL of toluene, and organic layers were then gathered. The gathered organic layer was washed with 180 mL of water three times. The resultant was filtrated, while washing the residue with toluene. The obtained filtrate was concentrated at 45° C. under reduced pressure, so as to obtain 22.4 g of 1,1-di-ethoxycarbonyl-2-vinylcyclopropane in the form of a crude product of a light yellow oily substance. This crude product contained 19.1 g of 1,1-di-ethoxycarbonyl-2-vinylcyclopropane (yield: 99%).

Example 8

Production of 1,1-di-ethoxycarbonyl-2-vinylcyclopropane 35.4 g (221 mmol) of diethyl malonate and 402 mL of toluene were added into a three-necked flask (1 L), and thereafter, 82.7 mL (211 mmol) of a 20% sodium ethoxide ethanol solution was added thereto as a base. The obtained mixture was stirred at room temperature for 0.5 hours, and 21.5 g of trans-1,4-dibromo-2-butene (101 mmol; a reagent manufactured by Sigma-Aldrich) was then added to the reaction solution. The obtained mixture was stirred at room temperature for 22 hours, and 241 mL of a 1 M sodium hydroxide aqueous solution was then added to the reaction solution. The mixture was stirred for 1 hour, and an organic layer was then separated. A water layer was re-extracted with 240 mL of toluene, and organic layers were then gathered. The gathered organic layer was washed with 240 mL of water three times. The resultant was filtered, while washing the residue with toluene. The obtained filtrate was concentrated at 45° C. under reduced pressure, so as to obtain 23.6 g of 1,1-di-ethoxycarbonyl-2-vinylcyclopropane in the form of a crude product of a light yellow oily substance. This crude product contained 21.2 g of 1,1-di-ethoxycarbonyl-2-vinylcyclopropane (yield: 99%).

Example 9

Production of
1,1-di-ethoxycarbonyl-2-vinylcyclopropane 35.2 g (220 mmol) of malonic acid diethyl esterdiethyl malonate and 400 mL of toluene were added into a three-necked flask (1 L), and thereafter, 82.3 mL (210 mmol) of a 20% sodium ethoxide ethanol solution was added thereto as a base. The obtained mixture was stirred at room temperature for 0.5 hours, and 12.5 g of trans-1,4-dichloro-2-butene (100 mmol; a reagent manufactured by Tokyo Chemical Industry Co., Ltd.) was then added to the reaction solution. The obtained mixture was stirred at room temperature for 5 days, and 240 mL of a 1 M sodium hydroxide aqueous solution was then added to the reaction solution. The mixture was stirred for 1 hour, and an organic layer was then separated. A water layer was re-extracted with 200 mL of toluene, and organic layers were then gathered. The gathered organic layer was washed with 200 mL of water three times, and the resultant was then filtered, while washing the residue with toluene. The obtained filtrate was concentrated at 45° C. under reduced pressure, so as to obtain 24.4 g of 1,1-di-ethoxycarbonyl-2-vinylcyclopropane in the form of a crude product of a light yellow oily substance. This crude product contained 19.5 g of 1,1-di-ethoxycarbonyl-2-vinylcyclopropane (yield: 92%).

Example 10

Production of
1,1-di-ethoxycarbonyl-2-vinylcyclopropane 80.2 g (501 mmol) of diethyl malonate and 850 mL of toluene were added into a four-necked flask (2 L), and thereafter, 191.7 mL (489 mmol) of a 20% sodium ethoxide ethanol solution was added thereto as a base. The obtained mixture was stirred at room temperature for 1.5 hours, and 51.0 g of trans-1,4-dibromo-2-butene (238 mmol; a reagent manufactured by Aldrich) was then added to the reaction solution. The obtained mixture was stirred at room temperature for 3 hours, and 537 mL of a 1 M sodium hydroxide aqueous solution was then added to the reaction solution. The mixture was stirred for 1 hour, and an organic layer was then separated. A water layer was re-extracted with 173 mL of toluene, and organic layers were then gathered. The gathered organic layer was washed with 86 mL of water twice, and it was then dried over anhydrous sodium sulfate, followed by filtration. The obtained filtrate was concentrated at 45° C. under reduced pressure, so as to obtain 53.3 g of 1,1-di-ethoxycarbonyl-2-vinylcyclopropane in the form of a crude product of a light yellow oily substance. This crude product contained 49.7 g of 1,1-di-ethoxycarbonyl-2-vinylcyclopropane (yield: 98.5%). In addition, it contained no diethyl malonates.

Example 11

Production of
1,1-di-ethoxycarbonyl-2-vinylcyclopropane 93.4 g (583 mmol) of diethyl malonate and 1000 mL of toluene 1000 mL were added into a four-necked flask (2 L), and thereafter, 223 mL (569 mmol) of a 20% sodium ethoxide ethanol solution was added thereto as a base. The obtained mixture was stirred at room temperature for 1.5 hours, and 59.4 g of trans-1,4-dibromo-2-butene (278 mmol; a reagent manufactured by Aldrich) was then added to the reaction solution. The obtained mixture was stirred at room temperature for 2 hours, and 109 mL (278 mmol) of a 20% sodium ethoxide ethanol solution was further added to the reaction solution. The mixture was stirred at room temperature for 1 hour, and 29.1 g of trans-1,4-dibromo-2-butene (136 mmol; a reagent manufactured by Aldrich) was then added thereto. The thus obtained mixture was stirred at room temperature for 4 hours, and 347 mL of a 1 M sodium hydroxide aqueous solution was then added thereto. The mixture was stirred for 14 hours, and an organic layer was then separated. Subsequently, the organic layer was washed with 132 mL of water twice, and it was then dried over anhydrous sodium sulfate, followed by filtration. The obtained filtrate was concentrated at 40° C. under reduced pressure, so as to obtain 99.3 g of 1,1-di-ethoxycarbonyl-2-vinylcyclopropane in the form of a crude product of a light yellow oily substance. This crude product contained 83.2 g of 1,1-di-ethoxycarbonyl-2-vinyl-cyclopropane (yield: 94.9%). In addition, it contained no diethyl malonates.

Example 12

Production of
(2S)-1,1-di-ethoxycarbonyl-2-vinylcyclopropane 250 mL of desalted water, 100 mL of *Rhizomucor miehei*-derived lipase (purchased from Sigma-Aldrich), and 50 mL of solution prepared by dissolving 1,1-di-ethoxycarbonyl-2-vinylcyclopropane which had been obtained in the same manner as that of Example 7 in dimethyl sulfoxide to a concentration of 100 g/L, were added to 100 mL of a 1 M Tris-HCl buffer (pH 7.5). Using a 1-L jar fermenter (manufactured by Able; model: BMJ), the obtained mixture was reacted at 30° C. at a stirring rate of 350 rpm for 42 hours. After completion of the reaction, 500 mL of the reaction solution was extracted with 1 L of ethyl acetate, and the quantification of 1,1-di-ethoxycarbonyl-2-vinylcyclopropane remaining in the reaction solution and the measurement of optical purity were then carried out. As for the quantification, the ethyl acetate extract was measured using gas chromatography (GC). As for the optical purity, an aliquot of the ethyl acetate extract was concentrated and dried, the obtained product was then dissolved in ethanol to prepare a solution, and the solution was then measured using liquid chromatography (HPLC). As a result of the analyses, the content of the (2S)-1,1-di-ethoxy-carbonyl-2-vinylcyclopropane was found to be 682 mg, and the optical purity was found to be 96.9% e.e. The obtained ethyl acetate solution was concentrated to a volume of 50 mL, and the concentrate was then washed with 30 mL of saturated sodium bicarbonate water three times, and then with 30 mL of brine once. The resultant was dried over anhydrous magnesium sulfate and was then concentrated.

HPLC optical purify analysis conditions are as follows. Column: Chiralpak IC (4.6 mm×250 mm; particle diameter: 5 μm) manufactured by Daicel Corporation, mobile phase: n-hexane 100/ethanol 2 (v/v), flow rate: 0.5 mL/min, column temperature: 35° C., UV: 210 nm Example 13

Production of (2S)-1,1-di-ethoxycarbonyl-2-vinylcyclopropane and (2R)-1,1-di-ethoxycarbonyl-2-vinylcyclopropane 1,1-di-ethoxycarbonyl-2-vinylcyclopropane, which had been obtained in the same manner as that of Example 7, was separated by liquid chromatography using Chiralpak IC (4.6 mm×250 mm; particle diameter: 5 μm) manufactured by Daicel Corporation. As a solvent, n-hexane 100/ethanol 2 (v/v) was used, and the flow rate of the solvent was set at 0.5 mL/min. With regard to the retention time of enantiomers at 35° C., it was 10.9 minutes in the case of the (2R) form, whereas it was 12.1 minutes in the case of the (2S) form.

Example 14

Production of (2S)-1,1-di-ethoxycarbonyl-2-vinylcyclopropane and (2R)-1,1-di-ethoxycarbonyl-2-vinylcyclopropane 1,1-di-ethoxycarbonyl-2-vinylcyclopropane, which had been obtained in the same manner as that of Example 10, was continuously separated by simulated moving bed liquid chromatography using four columns, TCI Chiral MB-S (4.6 mm×250 mm; particle diameter: 5 μm) manufactured by Tokyo Chemical Industry Co., Ltd. As a solvent, n-hexane 90/ethanol 10 (v/v) was used, and the flow rate of the solvent was set at 0.8 mL/min. The concentration of the raw material was set at 2.5 g/L. Both the (2R) form and the (2S) form had a purity of 98% and a recovery rate of 98%.

Example 15

Production of (1S,2S)/(1R,2R)-1-ethoxycarbonyl-2-vinylcyclopropanecarboxylic acid 4.22 g (19.9 mmol) of 1,1-di-ethoxycarbonyl-2-vinylcyclopropane, which had been obtained in the same manner as that of Example 7, and 25 mL of ethanol, were added into a 200-mL flask, and thereafter, 950 mg (23.7 mmol) of sodium hydroxide dissolved in 5.5 mL of water was added dropwise to the mixed solution under cooling on ice. The temperature was increased to room temperature, and the mixture was then stirred for 5 hours. Then, ethanol was distilled away. To the obtained solution, 20 mL of water was added, and the obtained mixture was then washed with 20 mL of tert-butylmethyl ether. Thereafter, 1 N hydrochloric acid was added to the water layer, so as to separate carboxylic acid. This aqueous solution was extracted with 20 mL of ethyl acetate three times, and the obtained organic layers were then gathered. The gathered organic layer was washed with 40 mL of brine, and it was then dried over anhydrous magnesium sulfate. The resultant was filtrated, while washing the residue with ethyl acetate, and the obtained filtrate was then concentrated at 35° C. under reduced pressure, so as to obtain 2.55 g of (1S,2S)/(1R,2R)-1-ethoxycarbonyl-2-vinylcyclopropanecarboxylic acid in the form of a colorless oily substance (yield: 69%). As a result of NMR analysis, the colorless oily substance was confirmed to be (1S,2S)/(1R,2R)-1-ethoxycarbonyl-2-vinylcyclopropanecarboxylic acid.

$^1$H-NMR (400 MHz, CDCl$_3$) δ1.33 (3H, t, J=7.3 Hz), 2.02 (1H, dd, J=4.5, 8.6 Hz), 2.19 (1H, dd, J=4.5, 9.1 Hz), 2.77 (1H, ddd, J=8.6, 8.6, 9.1 Hz), 4.24-4.37 (2H, m), 5.27 (1H, d, J=10.1 Hz), 5.42 (1H, d, J=16.9 Hz), 5.71 (1H, ddd, J=8.6, 10.1, 16.9 Hz)

Example 16

Production of (1S,2S)/(1R,2R)-1-ethoxycarbonyl-2-vinylcyclopropanecarboxylic acid 19.0 g (89.5 mmol) of 1,1-di-ethoxycarbonyl-2-vinylcyclopropane, which had been obtained in the same manner as that of Example 7, and 190 mL of ethanol, were added into a 500-mL flask, and thereafter, 89.5 mL (89.5 mmol) of a 1 M sodium hydroxide aqueous solution was added dropwise to the mixed solution under cooling on ice. The temperature was increased to room temperature, and the mixture was then stirred for 26 hours. Then, 4.48 mL (4.48 mmol) of a 1 M sodium hydroxide aqueous solution was added dropwise to the reaction solution, and the obtained mixture was further stirred for 7 hours. Thereafter, ethanol was concentrated. The obtained solution was washed with 95 mL of toluene twice, and 179 mL of 1 N hydrochloric acid was then added to the water layer so as to separate carboxylic acid. This aqueous solution was washed with 95 mL of toluene three times, and the obtained organic layers were then gathered. The gathered organic layer was washed with 95 mL of water three times, and the resultant was filtrated, while washing the residue with toluene. The obtained filtrate was then concentrated at 35° C. under reduced pressure, so as to obtain 13.7 g of (1S,2S)/(1R,2R)-1-ethoxycarbonyl-2-vinylcyclopropanecarboxylic acid in the form of a colorless oily substance (yield: 83%). As a result of NMR analysis, the colorless oily substance was confirmed to be (1S,2S)/(1R,2R)-1-ethoxycarbonyl-2-vinylcyclopropanecarboxylic acid.

Example 17

Production of (1S,2S)/(1R,2R)-1-ethoxycarbonyl-2-vinylcyclopropanecarboxylic acid 1.03 g (4.87 mmol) of 1,1-di-ethoxycarbonyl-2-vinylcyclopropane, which had been obtained in the same manner as that of Example 7, and 7.2 mL of ethanol, were added into a 50-mL flask, and thereafter, 4.87 mL (4.87 mmol) of a 1 M potassium hydroxide aqueous solution was added dropwise to the mixed solution under cooling on ice. The temperature was increased to room temperature, and the mixture was then stirred for 5 days. Then, ethanol was concentrated. The obtained solution was washed with 5 mL of toluene, and 1 N hydrochloric acid was then added to the water layer, so as to separate carboxylic acid. This aqueous solution was extracted with 5 mL of toluene three times, and the obtained organic layers were then gathered. The gathered organic layer was washed with 5 mL of water three times, and it was then dried over anhydrous magnesium sulfate. The resultant was filtrated, while washing the residue with toluene, and the obtained filtrate was then concentrated at 35° C. under reduced pressure, so as to obtain 671 mg of (1S,2S)/(1R,2R)-1-ethoxycarbonyl-2-vinylcyclopropanecarboxylic acid in the form of a colorless oily substance (yield: 75%). As a result of NMR analysis, the colorless oily substance was confirmed to be (1S,2S)/(1R,2R)-1-ethoxycarbonyl-2-vinylcyclopropanecarboxylic acid.

Example 18

Production of (1S,2S)-1-ethoxycarbonyl-2-vinylcyclopropanecarboxylic acid and production of (1R,2R)-1-ethoxycarbonyl-2-vinylcyclopropanecarboxylic acid (1S,2S)/(1R,2R)-1-ethoxycarbonyl-2-vinylcyclopropanecarboxylic acid, which had been obtained in the same manner as that of Example 16, was separated using TCI Chiral MB-S (4.6 mm×150 mm; particle diameter: 5 μm) manufactured by Tokyo Chemical Industry Co., Ltd. As a solvent, n-hexane 100/ethanol 2/trifluoroacetic acid 0.05 (v/v/v) was used, and the flow rate of the solvent was set at 0.5 mL/min. With regard to the retention time of enantiomers at 30° C., it was 8.6 minutes in the case of the (1S,2S) form, whereas it was 11.9 minutes in the case of the (1R,2R) form.

Example 19

Production of (1R,2S)/(1S,2R)-1-(tert-butoxycarbonyl)amino-1-ethoxycarbonyl-2-vinylcyclopropane 421.0 mg (2.29 mmol) of (1S,2S)/(1R,2R)-1-ethoxycarbonyl-2-vinylcyclopropanecarboxylic acid, which had been obtained in the same manner as that of Example 16, 10 mL of acetone, and 395 μL (2.93 mmol) of triethylamine, were added into a three-necked flask (100 mL), and thereafter, 384 μL (2.92 mmol) of isobutyl chloroformate was added dropwise to the mixed solution under cooling on ice. The obtained mixture was stirred for 30 minutes under cooling on ice, and 189.3 mg (2.91 mmol) of sodium azide was then added to the reaction solution, followed by stirring for 2 hours under cooling on ice.

Thereafter, to this mixture, 10 mL of toluene was added, and the obtained mixture was then washed with 10 mL of brine twice. The obtained organic layer was dried over anhydrous magnesium sulfate. The resultant was filtrated, while washing the residue with toluene, and the obtained filtrate was then concentrated at 35° C. under reduced pressure. An aliquot of toluene was distilled away, so as to obtain 10 mL of a solution.

This toluene solution was added into a three-necked flask (100 mL), and thereafter, 1 mL of anhydrous acetic acid and 4 mL of tert-butyl alcohol were added thereto, followed by stirring for 1 hour. Thereafter, the reaction solution was stirred at 80° C. for 2 hours. The obtained mixture was concentrated under reduced pressure, and the residue was then purified by silica gel column chromatography (silica gel: 10 g; hexane-ethyl acetate=20:1-10:1-3:1), so as to obtain 368.9 mg of (1R,2S)/(1S,2R)-1-(tert-butoxycarbonyl)amino-1-ethoxycarbonyl-2-vinylcyclopropane in the form of a yellow oily substance (yield: 63%). As a result of NMR analysis, the yellow oily substance was confirmed to be (1R,2S)/(1S,2R)-1-(tert-butoxycarbonyl)amino-1-ethoxycarbonyl-2-vinylcyclopropane.

$^1$H-NMR (400 MHz, a mixture of DMSO-d6 and rotational isomers (3:1))

δ1.13-1.19 (3H, m), 1.28 (1H, dd, J=5.0, 9.1 Hz), 1.35 (2.3H, s), 1.38 (6.7H, s), 1.56 (1H, dd, J=5.0, 7.8 Hz), 2. 10 (1H, ddd, J=7.8, 9.1, 9.6 Hz), 3.97-4.14 (2H, m), 5.06 (1H, dd, J=2.0, 10.3 Hz), 5.23 (1H, d, J=17.2 Hz), 5.57-5.66 (1H, ddd, J=9.6, 10.3, 17.2 Hz), 7.32 (0.75H, brs), 7.67 (0.25H, brs).

Example 20

Production of (1R,2S)/(1S,2R)-1-amino-1-ethoxycarbonyl-2-vinylcyclopropane using (1R,2S)/(1S,2R)-1-(tert-butoxycarbonyl)amino-1-ethoxycarbonyl-2-vinylcyclopropane as raw material 929 mg (3.64 mmol) of (1R,2S)/(1S,2R)-1-(tert-butoxycarbonyl)amino-1-ethoxycarbonyl-2-vinylcyclopropane, which had been obtained in the same manner as that of Example 19, and 0.38 mL of ethyl acetate, were added into an eggplant-shaped flask (100 mL), and the obtained mixture was then cooled to 10° C. Then, 0.42 g (4.28 mmol) of sulfuric acid dissolved in 0.78 mL of ethyl acetate was added dropwise to the reaction solution. The obtained mixture was stirred at room temperature for 30 minutes, and then at 50° C. for 1 hour. The reaction solution was concentrated, and 10 mL of water was then added to the concentrate. Thereafter, a 1 N sodium hydroxide aqueous solution was added to the water layer, so as to separate amine. This aqueous solution was extracted with 10 mL of tert-butylmethyl ether twice, and the obtained tert-butylmethyl ether layers were gathered. The gathered layer was washed with 10 mL of brine, and it was then dried over anhydrous magnesium sulfate. The resultant was filtrated, while washing the residue with tert-butylmethyl ether, and the obtained filtrate was then concentrated at 35° C. under reduced pressure, so as to obtain 482 mg of (1R,2S)/(1S,2R)-1-amino-1-ethoxycarbonyl-2-vinylcyclopropane in the form of a colorless oily substance (yield: 79%). As a result of NMR analysis, the yellow oily substance was confirmed to be (1R,2S)/(1S,2R)-1-amino-1-ethoxycarbonyl-2-vinylcyclopropane.

$^1$H-NMR (400 MHz, CDCl$_3$) δ1.28 (3H, t, J=7.3 Hz), 1.33 (1H, dd, J=4.8, 9.4 Hz), 1.55 (1H, dd, J=4.8, 7.4 Hz), 1.99 (2H, br. s), 2.02 (1H, ddd, J=8.7, 9.4, 9.4 Hz), 4.23-4.12 (2H, m), 5.08 (1H, dd, J=1.76, 10.4 Hz), 5.21 (1H, dd, J=1.76, 17.2 Hz), 5.71 (1H, ddd, J=9.4, 10.4, 17.2 Hz)

Example 21

Production of (1R,2S)/(1S,2R)-1-amino-1-ethoxycarbonyl-2-vinylcyclopropane hemisulfate salt 482 mg (3.11 mmol) of (1R,2S)/(1S,2R)-1-amino-1-ethoxycarbonyl-2-vinylcyclopropane, which had been obtained in Example 20, and 1.0 mL of ethyl acetate, were added into an eggplant-shaped flask (100 mL). Thereafter, 176 mg (1.79 mmol) of sulfuric acid dissolved in 1.0 mL of ethyl acetate was added dropwise to the mixed solution, followed by stirring. The obtained powder was filtrated, while washing the residue with ethyl acetate, so as to obtain 357 mg of (1R,2S)/(1S,2R)-1-amino-1-ethoxycarbonyl-2-vinylcyclopropane hemisulfate salt in the form of a white powder (yield: 43%). As a result of NMR analysis, the white powder was confirmed to be (1R,2S)/(1S,2R)-1-amino-1-ethoxycarbonyl-2-vinylcyclopropane hemisulfate salt.

$^1$H-NMR (400 MHz, DMSO-d6) δ1.21 (3H, t, J=7.1 Hz), 1.44 (1H, dd, J=5.3, 9.6 Hz), 1.53 (1H, dd, J=5.3, 7. 6 Hz), 2.02 (1H, ddd, J=7.6, 9.1, 9.6 Hz), 4.20-4.09 (2H, m), 5.08 (1H, dd, J=1.76, 10.1 Hz), 5.09 (1H, dd, J=1. 76, 17.2 Hz), 5.28 (1H, ddd, J=9.1, 10.1, 17.2 Hz)

Example 22

Production of (1R,2S)/(1S,2R)-1-amino-1-ethoxycarbonyl-2-vinylcyclopropane using (1S,2S)/(1R,2R)-1-ethoxycarbonyl-2-vinylcyclopropanecarboxylic acid as raw material 9.66 g (52.4 mmol) of (1S,2S)/(1R,2R)-1-ethoxycarbonyl-2-vinylcyclopropanecarboxylic acid, which had been obtained in the same manner as that of Example 16, 150 mL of toluene, and 8.48 mL (62.9 mmol) of triethylamine, were added into a three-necked flask (500 mL). Thereafter, 5.99 mL (62.9 mmol) of ethyl chloroformate was added dropwise to the mixed solution under cooling on ice. The obtained mixture was stirred for 1 hour under cooling on ice, and 4.48 g (68.9 mmol) of sodium azide was then added to the reaction solution. The obtained mixture was stirred for 2 hours under cooling on ice. This mixture was washed with 30 mL of brine twice, and the obtained toluene layer was then dried over anhydrous magnesium sulfate. The resultant was filtrated, while washing the residue with toluene, and 4.5 g of Molecular Sieves 4A Powder was then added to the obtained filtrate. The obtained mixture was dried at room temperature for 12 hours, and it was then filtrated to remove the Molecular Sieves. The obtained filtrate was added into a three-necked flask (500 mL), and it was then stirred at 80° C. for 3 hours. Thereafter, this toluene solution was cooled to room temperature, and it was then added dropwise to a three-necked flask (500 mL), which contained a mixed solution of 7.70 g (78.5 mmol) of sulfuric acid, 4.7 g of water and 48 mL of acetone. The obtained mixture was stirred at room temperature for 96 hours. Thereafter, 50 mL of water was added to the reaction solution, the mixture was then stirred, and the toluene layer was then removed. Then, a 1 N sodium hydroxide aqueous solution was added to the water layer, so as to separate amine. This aqueous solution was extracted with 50 mL of ethyl acetate twice, and the obtained ethyl acetate layers were gathered. The gathered ethyl acetate layer was washed with 50 mL of brine, and it was then dried over anhydrous magnesium sulfate. The resultant was filtrated, while washing the residue with ethyl acetate, so as to obtain an ethyl acetate solution of (1R,2S)/(1S,2R)-1-amino-1-ethoxycarbonyl-2-vinylcyclopropane. It was confirmed by NMR analysis that the aforementioned solution contained (1R,2S)/(1S,2R)-1-amino-1-ethoxycarbonyl-2-vinylcyclopropane.

$^1$H-NMR (400 MHz, CDCl$_3$) δ1.28 (3H, t, J=7.3 Hz), 1.33 (1H, dd, J=4.8, 9.4 Hz), 1.55 (1H, dd, J=4.8, 7.4 Hz), 1.99 (2H, br. s), 2.02 (1H, ddd, J=8.7, 9.4, 9.4 Hz), 4.23-4.12 (2H, m), 5.08 (1H, dd, J=1.76, 10.4 Hz), 5.21 (1H, dd, J=1.76, 17.2 Hz), 5.71 (1H, ddd, J=9.4, 10.4, 17.2 Hz)

Example 23

Production of (1R,2S)/(1S,2R)-1-amino-1-ethoxycarbonyl-2-vinylcyclopropane hemisulfate salt The ethyl acetate solution of (1R,2S)/(1S,2R)-1-amino-1-ethoxycarbonyl-2-vinylcyclopropane, which had been obtained in Example 22, was added into an eggplant-shaped flask (300 mL), and 2.02 g (20.6 mmol) of sulfuric acid was then added dropwise to the solution, followed by stirring. The obtained powder was filtrated, while washing the residue with ethyl acetate, so as to obtain 6.31 g (yield: 59%) of (1R,2S)/(1S,2R)-1-amino-1-ethoxycarbonyl-2-vinylcyclopropane in the form of a white powder. As a result of NMR analysis, the white powder was confirmed to be (1R,2S)/(1S,2R)-1-amino-1-ethoxycarbonyl-2-vinylcyclopropane hemisulfate salt.

$^1$H-NMR (400 MHz, DMSO-d6) δ1.21 (3H, t, J=7.1 Hz), 1.44 (1H, dd, J=5.3, 9.6 Hz), 1.53 (1H, dd, J=5.3, 7.6 Hz), 2.02 (1H, ddd, J=7.6, 9.1, 9.6 Hz), 4.20-4.09 (2H, m), 5.08 (1H, dd, J=1.76, 10.1 Hz), 5.09 (1H, dd, J=1.76, 17.2 Hz), 5.28 (1H, ddd, J=9.1, 10.1, 17.2 Hz)

Example 24

Production of (1S,2S)-1-ethoxycarbonyl-2-vinylcyclopropanecarboxylic acid 682 mg (3.21 mmol) of (2S)-1,1-di-ethoxycarbonyl-2-vinylcyclopropane, which had been obtained in Example 12, and 7 ml of ethanol, were added into a 300-mL flask, and thereafter, 2.58 g (16.1 mmol) of a 25% sodium hydroxide aqueous solution was added dropwise to the mixed solution under cooling on ice. The temperature of the obtained solution was increased to room temperature, and the solution was then stirred for 9 hours. Thereafter, ethanol was distilled away. To the obtained solution, 20 mL of water was added, and the mixture was then washed with 30 mL of tert-butylmethyl ether twice. Then, 1 N hydrochloric acid was added to the water layer, so as to separate carboxylic acid. This aqueous solution was extracted with 20 mL of toluene three times, and the obtained organic layers were then gathered. The gathered organic layer was washed with 30 mL of brine, and it was then dried over anhydrous magnesium sulfate. The resultant was filtrated, while washing the residue with ethyl acetate, and the obtained filtrate was then concentrated at 35° C. under reduced pressure, so as to obtain 526 mg of (1S,2S)-1-ethoxycarbonyl-2-vinylcyclopropanecarboxylic acid in the form of a colorless oily substance (yield: 89%). As a result of NMR analysis, the colorless oily substance was confirmed to be (1S,2S)-1-ethoxycarbonyl-2-vinylcyclopropanecarboxylic acid.

$^1$H-NMR (400 MHz, CDCl$_3$) δ1.33 (3H, t, J=7.3 Hz), 2.02 (1H, dd, J=4.5, 8.6 Hz), 2.19 (1H, dd, J=4.5, 9.1 Hz), 2.77 (1H, ddd, J=8.6, 8.6, 9.1 Hz), 4.24-4.37 (2H, m), 5.27 (1H, d, J=10.1 Hz), 5.42 (1H, d, J=16.9 Hz), 5.71 (1H, ddd, J=8.6, 10.1, 16.9 Hz)

Example 25

Production of (1R,2S)-1-amino-1-ethoxycarbonyl-2-vinylcyclopropane 526 mg (2.86 mmol) of (1S,2S)-1-ethoxycarbonyl-2-vinylcyclopropanecarboxylic acid, which had been obtained in Example 24, 6 mL of toluene, and 502 μL (3.72 mmol) of triethylamine, were added into a three-necked flask (50 mL). Thereafter, 354 μL (3.72 mmol) of ethyl chloroformate was added dropwise to the mixed solution under cooling on ice. The obtained mixture was stirred for 30 minutes under cooling on ice, 240 mg (3.72 mmol) of sodium azide was then added to the reaction solution. The mixture was stirred for 2 hours under cooling on ice. Thereafter, this mixture was washed with 10 mL of brine twice, and the obtained toluene layer was then dried over anhydrous magnesium sulfate. The resultant was filtrated, while washing the residue with toluene, and 270 mg of Molecular Sieves 4A Powder was then added to the obtained filtrate. The obtained mixture was dried at room temperature for 24 hours, and it was then filtrated to remove the Molecular Sieves. The obtained filtrate was added into a three-necked flask (50 mL), and it was then stirred at 80° C. for 3 hours. Thereafter, this toluene solution was cooled to room temperature, and it was then added dropwise to an eggplant-shaped flask (50 mL), which contained a mixed solution of 7.70 g (78.5 mmol) of sulfuric acid, 250 mg of water and 2.6 mL of acetone. The obtained mixture was stirred at room temperature for 24 hours. Thereafter, 10 mL of water was added to the reaction solution, and the toluene layer was then removed. Then, a 50% sodium hydroxide aqueous solution was added to the water layer, so as to separate amine. This aqueous solution was extracted with 10 mL of tert-butylmethyl ether twice, and the obtained toluene layers were gathered. The gathered toluene layer was washed with 10 mL of brine, and it was then dried over anhydrous magnesium sulfate. The resultant was filtrated, while washing the residue with tert-butylmethyl ether, and the obtained filtrate was concentrated at 35° C. under reduced pressure, so that an aliquot of the tert-butylmethyl ether was distilled away. The quantification of (1R,2S)-1-amino-1-ethoxycarbonyl-2-vinylcyclopropane in the reaction solution and the measurement of optical purity were carried out. Quantification was carried out on the tert-butylmethyl ether solution, using NMR. As for the measurement of the optical purity, the tert-butylmethyl ether solution was dissolved in ethanol, and the optical purity was then measured using liquid chromatography (HPLC). As a result of the analyses, the content of the (1R,2S)-1-amino-1-ethoxycarbonyl-2-vinylcyclopropan was found to be 625 mg, and the optical purity was found to be 94.5% e.e.

HPLC measurement conditions are as follows.
Column: Chiralpak AD-RH (4.6 mm×150 mm; particle diameter: 5 μm) manufactured by Daicel Corporation, mobile phase: water 30/0.1% diethylamine-containing methanol 70 (v/v), flow rate: 0.5 mL/min, column temperature: 40° C., UV: 210 nm $^1$H-NMR (400 MHz, CDCl$_3$) δ1.28 (3H, t, J=7.3 Hz), 1.33 (1H, dd, J=4.8, 9.4 Hz), 1.55 (1H, dd, J=4.8, 7.4 Hz), 1.99 (2H, br. s), 2.02 (1H, ddd, J=8.7, 9.4, 9.4 Hz), 4.23-4.12 (2H, m), 5.08 (1H, dd, J=1.76, 10.4 Hz), 5.21 (1H, dd, J=1.76, 17.2 Hz), 5.71 (1H, ddd, J=9.4, 10.4, 17.2 Hz)

Example 26

Production of (1R,2S)-1-amino-1-ethoxycarbonyl-2-vinylcyclopropane hemisulfate salt The (1R,2S)-1-amino-1-ethoxycarbonyl-2-vinylcyclopropane obtained in Example 25 was subjected to the same operations as those of Example 23, so as to produce (1R,2S)-1-amino-1-ethoxycarbonyl-2-vinylcyclopropane hemisulfate salt.

HPLC optical purify analysis conditions are as follows.
Column: Chiralpak AD-RH (4.6 mm×150 mm; particle diameter: 5 μm) manufactured by Daicel Corporation, mobile phase: water 30/0.1% diethylamine-containing methanol 70 (v/v), flow rate: 0.5 mL/min, column temperature: 40° C., UV: 210 nm $^1$H-NMR (400 MHz, DMSO-d6) δ1.21 (3H, t, J=7.1 Hz), 1.44 (1H, dd, J=5.3, 9.6 Hz), 1.53 (1H, dd, J=5.3, 7. 6 Hz), 2.02 (1H, ddd, J=7.6, 9.1, 9.6 Hz), 4.20-4.09 (2H, m), 5.08 (1H, dd, J=1.76, 10.1 Hz), 5.09 (1H, dd, J=1. 76, 17.2 Hz), 5.28 (1H, ddd, J=9.1, 10.1, 17.2 Hz)

Example 27

Production of (1S,2S)-1-ethoxycarbonyl-2-vinylcyclopropanecarboxylic acid (Biocatalytic Process)

40 mL of a 1 M potassium phosphate buffer (pH 7.0), 331 mL of desalted water, 12.58 g of the 1,1-di-ethoxycarbonyl-2-vinylcyclopropane obtained in Example 10, and 6 g of a wet cell mass of *Escherichia coli* clone No. 26 isolated in Reference Example 2, were mixed in a 1-L jar fermenter, and the obtained mixture was then reacted at 30° C. at pH 7.0 at a stirring rate of 500 rpm for 22 hours. After completion of the reaction, the cell mass and the cell residue were removed from the reaction solution, and 80 mL of toluene was then added to the remaining solution. The mixed solution was stirred at room temperature for 20 minutes, and the toluene layer was then separated, and the remaining 1,1-di-ethoxycarbonyl-2-vinylcyclopropane was then removed. To the obtained water layer, 6 N sulfuric acid was added, so that the pH of the solution was adjusted to pH 2.0. Thereafter, 80 mL of toluene was added to the solution, and the obtained mixture was then stirred at room temperature for 20 minutes, so as to obtain a toluene layer, which contained (1S,2S)-1-ethoxycarbonyl-2-vinylcyclopropanecarboxylic acid. To the thus obtained water layer, 80 mL of toluene was added again, and the obtained mixture was then stirred at room temperature for 20 minutes, to obtain a toluene layer containing (1S,2S)-1-ethoxycarbonyl-2-vinylcyclopropanecarboxylic acid. The purity and optical purity of the obtained toluene layer were measured by HPLC analysis. As a result, the content of the (1S,2S)-1-ethoxycarbonyl-2-vinylcyclopropanecarboxylic acid was found to be 4.22 g (0.023 mol, yield: 40.5%), and the optical purity was found to be 98.4% e.e.

HPLC purity analysis conditions are as follows.
Column: Nacalai Tesque COSMOSIL5C18-MSII (4.6 mm×250 mm,), mobile phase: a mixed solution of 0.1% formic acid solution and acetonitrile (wherein the concentration of acetonitrile was increased from 25% to 70% over 20 minutes in a linear gradient manner), flow rate: 1.0 mL/min, column temperature: 40° C., UV: 220 nm In addition, HPLC optical purity analysis conditions are as follows.
Column: CHIRALPAK AD-3 (4.6 mm×250 mm; particle diameter: 3 μm) manufactured by Daicel Corporation, mobile phase: 95% hexane/5% ethanol/0.1% trifluoroacetic acid, flow rate: 0.8 mL/min, column temperature: 30° C., UV: 220 nm Example 28

Production of (1R,2S)-1-amino-1-ethoxycarbonyl-2-vinylcyclopropane p-toluenesulfonate 3.7387 kg of a toluene solution containing 381.34 g (2.0704 mol) of the (1S,2S)-1-ethoxycarbonyl-2-vinylcyclopropanecarboxylic acid obtained in Example 27 and 261.71 g (1.4209 mol) of (1R,2R)-1-ethoxycarbonyl-2-vinylcyclopropanecarboxylic acid was added into a 5-L round-bottom flask, and it was then cooled on ice. Then, 166.89 g of toluene was added to this solution, and the obtained mixture was stirred. Thereafter, 370.94 g (3.6658 mol) of triethylamine was added dropwise to the reaction solution over 45 minutes. At the same time, 397.80 g (3.6658 mol) of ethyl chloroformate and 868.08 g of toluene were added into a 10-L separable flask, and the mixture was stirred and was then cooled to 0° C. To this solution, a toluene solution of triethylamine salts of (1R, 2S)/(1S,2R)-1-amino-1-ethoxycarbonyl-2-vinylcyclopropane, which had been previously prepared, was added dropwise over 2 hours.

Thereafter, an aqueous solution prepared by mixing 249.65 g (3.8404 mol) of sodium azide with 1.2861 kg of water was added dropwise to the mixed solution over 35 minutes. Subsequently, a hydrochloric acid solution prepared by mixing 109.25 g (1.0474 mol) of 35% hydrochloric acid with 192.92 g of water was added dropwise to the mixed solution over 1 hour 20 minutes. The obtained mixture was stirred for 14 hours. After completion of the reaction, a water layer was removed, and a toluene layer was washed with 1350 g of 5% sodium bicarbonate water twice, and then with 772.4 g of a 20% saline once. To the obtained toluene layer, 160.86 g of anhydrous magnesium sulfate was added, and the obtained mixture was then stirred at 0° C. for 30 minutes, followed by filtration. Magnesium sulfate was washed with 222.27 g of toluene, and the washing solution was mixed with the filtrate. To this toluene solution, 64.36 g of Molecular Sieves 4A was added, and the mixed solution was then stirred at 0° C. for 8 hours, followed by filtration. The Molecular Sieves was washed with 222.50 g of toluene, and the washing solution was mixed with the filtrate, so as to obtain a toluene solution of (1R,2S)/(1R,2R)-1-(ethoxycarbonyl)-2-vinylcyclopropane carboxyl azide.

1.1124 kg of toluene was added into a 10-L separable flask, and it was then heated to 80° C. The toluene solution of (1R,2S)/(1R,2R)-1-(ethoxycarbonyl)-2-vinylcyclopropane carboxyl azide, which had been previously prepared, was added dropwise to the aforementioned toluene over 3 hours. After completion of the dropwise addition, the obtained mixture was further stirred at 80° C. for 2.5 hours, and it was then cooled to 20° C.

To the obtained solution, 373.16 g (1.9619 mol) of p-toluenesulfonic acid monohydrate and 882.7 g of acetone were successively added. The obtained mixture was stirred at 20° C. for 9 hours, at 30° C. for 3 hours, at 40° C. for 2 hours, at 50° C. for 2 hours, and then at 60° C. for 3 hours. Thereafter, the reaction solution was concentrated to a volume of 2.3 L, and the concentrate was then heated to 50° C. To this concentrate, 4.4357 kg of diisopropyl ether was added dropwise over 40 minutes, and it was then cooled to 20° C. over 2 hours 20 minutes. Thereafter, the resultant was aged at 20° C. for 2 hours, and the generated crystal was then collected by filtration. The crystal was washed with 443.49 g of diisopropyl ether, and was then dried under reduced pressure under nitrogen current, so as to obtain 656.1 g of crude (1R,2S)/(1S,2R)-1-amino-1-ethoxycarbonyl-2-vinylcyclopropane p-toluenesulfonate in the form of a yellow-brown crystal. As a result of analysis by HPLC, the content of the (1R,2S)-1-amino-1-ethoxycarbonyl-2-vinylcyclopropane p-toluenesulfonate was found to be 518.29 g (1.583 mol, yield: 76.5%), and the optical purity was found to be 99.2% e.e.

HPLC chemical purity analysis conditions are as follows.
Column: L-column (4.6 mm×150 mm; particle diameter: 5 μm) manufactured by Chemicals Evaluation and Research Institute, Japan, mobile phase: 40% 30 mM sodium dihydrogen phosphate aqueous solution/60% acetonitrile
Flow rate: 1.0 mL/min, column temperature: 40° C., UV: 210 nm In addition, HPLC optical purify analysis conditions are as follows.
Column: Chiralpak AD-RH (4.6 mm×150 mm; particle diameter: 5 μm) manufactured by Daicel Corporation, mobile phase: water 30/0.1% diethylamine-containing methanol 70 (v/v), flow rate: 0.5 mL/min, column temperature: 40° C., UV: 210 nm $^1$H-NMR (400 MHz, CDCl$_3$) δ1.18 (3H, t, J=7.3 Hz), 1.56 (1H, dd, J=6.6, 8.3 Hz), 1.92 (1H, dd, J=6.6, 10.1 Hz), 2.55 (1H, ddd, J=8.3, 10.1, 10.1 Hz), 4.04-4.17 (2H, m), 5.09 (1H, dd, J=1.24, 10.1 Hz), 5.20 (1H, dd, J=1.24, 17.7 Hz), 5.60 (1H, ddd, J=8.3, 10.1, 17.2 Hz)

Example 29

Recrystallization of (1R,2S)-1-amino-1-ethoxycarbonyl-2-vinylcyclopropane p-toluenesulfonate 517.37 g (1.580 mol) out of the crude (1R,2S)-1-amino-1-ethoxycarbonyl-2-vinylcyclopropane p-toluenesulfonate obtained in Example 28 was placed in a 10-L separable flask, and 2241.9 g of toluene was then added thereto. The obtained mixture was heated to 70° C., so that the aforementioned compound was dissolved in toluene. The obtained solution was cooled to 5° C. over 5 hours and was then aged at 5° C. for 3 hours. The generated crystal was collected by filtration. The crystal was washed with 448.3 g of toluene and was then dried under reduced pressure under nitrogen current, so as to obtain 499.7 g of pure (1R,2S)-1-amino-1-ethoxycarbonyl-2-vinylcyclopropane p-toluenesulfonate in the form of a yellow-brown crystal. As a result of analysis by HPLC, the content of the (1R,2S)-1-amino-1-ethoxycarbonyl-2-vinylcyclopropane p-toluenesulfonate was found to be 485.8 g (1.484 mol, yield: 93.9%), and the optical purity was found to be 99.5% e.e.

HPLC chemical purity analysis conditions are as follows.
Column: L-column (4.6 mm×150 mm; particle diameter: 5 μm) manufactured by Chemicals Evaluation and Research Institute, Japan, mobile phase: 40% 30 mM sodium dihydrogen phosphate aqueous solution/60% acetonitrile
Flow rate: 1.0 mL/min, column temperature: 40° C., UV: 210 nm In addition, HPLC optical purify analysis conditions are as follows.
Column: Chiralpak AD-RH (4.6 mm×150 mm; particle diameter: 5 μm) manufactured by Daicel Corporation, mobile phase: water 30/0.1% diethylamine-containing methanol 70 (v/v), flow rate: 0.5 mL/min, column temperature: 40° C., UV: 210 nm Example 30

Production of (1R,2S)-1-amino-1-ethoxycarbonyl-2-vinylcyclopropane 498.4 g (content: 484.49 g, 1.48 mol) out of the (1R,2S)-1-amino-1-ethoxycarbonyl-2-vinylcyclopropane p-toluenesulfonate obtained in Example 29 and 2.1915 kg of ethyl acetate were added into a 10-L separable flask, and the obtained mixture was then cooled to 6° C. To this mixture, a potassium bicarbonate aqueous solution consisting of 220.04 g (2.2259 mol) of potassium bicarbonate and 971.7 g of water was added dropwise over 20 minutes, so as to separate (1R,2S)-1-amino-1-ethoxycarbonyl-2-vinylcyclopropane. The mixture was stirred for 1 hour, while maintaining the temperature at 6° C., so that an ethyl acetate layer was separated. To a water layer, 48.54 g of sodium chloride and 876.8 g of ethyl acetate were added, and the obtained mixture was then stirred at 6° C. for 1 hour 20 minutes. Thereafter, an ethyl acetate layer was separated. After this operation, 438.3 g of ethyl acetate was added to the obtained water layer, the obtained mixture was then stirred at 26° C. for 1 hour, and an ethyl acetate layer was then separated. This operation was repeatedly carried out three times. All of the ethyl acetate layers were gathered in a 10-L separable flask, and the gathered layer was then cooled to 6° C. Then, 121.47 g of sodium sulfate was added thereto, and the obtained mixture was then stirred for 30 minutes. The sodium sulfate was then removed by filtration. The sodium sulfate was washed with 438.3 g of ethyl acetate, and the washing solution was then mixed with the filtrate, so as to obtain an ethyl acetate solution of (1R,2S)-1-amino-1-ethoxycarbonyl-2-vinylcyclopropane. As a result of analysis by HPLC, the content of the (1R,2S)-1-amino-1-ethoxycarbonyl-2-vinylcyclopropane was found to be 212.86 g (yield: 95.1%).

HPLC chemical purity analysis conditions are as follows.
Column: L-column (4.6 mm×150 mm; particle diameter: 5 µm) manufactured by Chemicals Evaluation and Research Institute, Japan, mobile phase: 40% 30 mM sodium dihydrogen phosphate aqueous solution/60% acetonitrile
Flow rate: 1.0 mL/min, column temperature: 40° C., UV: 210 nm Example 31

Production of (1R,2S)-1-amino-1-ethoxycarbonyl-2-vinylcyclopropane hemisulfate salt An ethyl acetate solution of the (1R,2S)-1-amino-1-ethoxycarbonyl-2-vinylcyclopropane obtained in Example 30 was cooled to 2° C., and then, using a dropping funnel, 69.34 g (1.372 mmol) of 97% sulfuric acid was added dropwise thereto over 50 minutes. Sulfuric acid remaining in the dropping funnel was transferred to the mixture using 87.64 g of ethyl acetate. Thereafter, the temperature of the mixture was increased to 40° C., and the mixture was then concentrated under reduced pressure to result in a liquid amount of 3.2 L. To the obtained concentrate, 1.2606 kg of toluene was added, and the mixture was then cooled to 0° C. over 2 hours. After the mixture had been kept cold at 0° C. for 2 hours, the generated crystal was collected by filtration. The obtained crystal was washed with 420.3 g of toluene, and it was then dried at room temperature for 2 hours under nitrogen current. Thereafter, it was dried under reduced pressure at 40° C. for 10 hours, so as to obtain 267.79 g of (1R,2S)-1-amino-1-ethoxycarbonyl-2-vinylcyclopropane hemisulfate salt in the form of a white crystal.

As a result of HPLC analysis, the content of the (1R,2S)-1-amino-1-ethoxycarbonyl-2-vinylcyclopropane hemisulfate salt was found to be 267.79 g (yield: 95.6%), and the optical purity was found to be 99.2% e.e.

HPLC chemical purity analysis conditions are as follows.
Column: L-column (4.6 mm×150 mm; particle diameter: 5 µm) manufactured by Chemicals Evaluation and Research Institute, Japan, mobile phase: 40% 30 mM sodium dihydrogen phosphate aqueous solution/60% acetonitrile
Flow rate: 1.0 mL/min, column temperature: 40° C., UV: 210 nm
In addition, HPLC optical purify analysis conditions are as follows.
Column: Chiralpak AD-RH (4.6 mm×150 mm; particle diameter: 5 µm) manufactured by Daicel Corporation, mobile phase: water 30/0.1% diethylamine-containing methanol 70 (v/v), flow rate: 0.5 mL/min, column temperature: 40° C., UV: 210 nm Reference Example 1

Cloning of para-Nitrobenzyl Esterase Gene (pnbA3027; SEQ ID NO. 2)

(1) Gene Cloning

*Bacillus subtilis* strain, NBRC3027, were cultivated overnight in liquid media designated by the culture collection. Thereafter, chromosomal DNA was prepared from each of the obtained cell masses, using DNeasy Blood & Tissue Kit (manufactured by QIAGEN).

Based on a gene sequence (hereinafter referred to as pnbA23857, SEQ ID NO. 2) encoding para-nitrobenzyl esterase derived from *Bacillus subtilis* ATCC23857 whose genome sequence had been known (hereinafter referred to as PNBE23857, GenBank Accession No. ZP_03593235, SEQ ID NO. 1), primers for amplifying a full-length para-nitrobenzyl esterase gene were designed and synthesized. The nucleotide sequences of the two primers are shown in SEQ ID NO. 3 (pnbA F) and SEQ ID NO. 4 (pnbA R) in the sequence listing, respectively.

Using the prepared chromosomal DNA as a template, and also using pnbA F and pnbA R as primers, a DNA fragment with a size of approximately 1.5 kbp was amplified by PCR.

(2) Preparation of Expression Vector

Using the plasmid pKV32 (JP Patent Publication (Kokai) No. 2005-34025 A) as a template, and also using the primer (pKVXmaIFW) shown in SEQ ID NO. 5 and the primer (pKVXmaIRV) shown in SEQ ID NO. 6, a fragment with a size of approximately 4 kbp was amplified by PCR. The amplified fragment was digested with XmaI, and thereafter, using Ligation-Convenience Kit (manufactured by Nippon Gene Co., Ltd.), it was subjected to self ligation. The obtained plasmid was named as pKW32.

(3) Preparation of Expression Plasmid

In accordance with an ordinary method, the DNA fragment obtained in (1) above was introduced into the cloning vector pKW32 prepared in (2) above. Hereinafter, the obtained plasmid was referred to as ppnbA3027.

The DNA sequence inserted into the plasmid was analyzed, and as a result, it was confirmed that it contained a gene comprising 1467-bp ORF. The obtained gene was named as pnbA3027, and the sequence of the gene was as shown in SEQ ID NO. 7. The amino acid sequence encoded by this DNA sequence was named as PNBE3027, and it was as shown in SEQ ID NO. 8. The amino acid sequence PNBE3027 showed sequence identity of 90s % with the known sequence PNBE23857.

Reference Example 2

Modification of para-Nitrobenzyl Esterase Gene by Introduction of Mutation

Using the plasmid ppnbA3027 obtained in Reference Example 1 as a template, and also using the primer (L70FW) shown in SEQ ID NO. 9 in the sequence listing and the primer (L70RV) shown in SEQ ID NO. 10 in the sequence listing, QuikChange Multi Site-Directed Mutagenesis Kit (manufactured by Stratagene) was employed to introduce random mutation into a nucleotide encoding leucine at amino acid number 70 in the aforementioned plasmid. In the same way, using the primer (L313FW) shown in SEQ ID NO. 11 in the sequence listing and the primer (L313RV) shown in SEQ ID NO. 12 in the sequence listing, random mutation was introduced into a nucleotide encoding the leucine residue at amino acid number 313, in the aforementioned plasmid; and using the primer (L270L273FW) shown in SEQ ID NO. 13 in the sequence listing and the primer (L270L273RV) shown in SEQ ID NO. 14 in the sequence listing, random mutation was introduced into nucleotides encoding the leucine residues at amino acid numbers 270 and 273, in the aforementioned plasmid. Using the thus obtained mutation-introduced plasmid, *Escherichia coli* JM109 (manufactured by Takara Bio, Inc.) was transformed according to an ordinary method.

Thereafter, clone No. 26 was isolated from the thus obtained recombinant *Escherichia coli*, and the DNA sequence inserted into the plasmid possessed by the present clone was then analyzed. As a result, the sequence (named as pnbA3027-26) was as shown in SEQ ID NO. 15. The amino acid sequence encoded by the present DNA sequence was named as PNBE3027-26. The amino acid sequence was as shown in SEQ ID NO. 16.

Reference Example 3

Production of 1,1-di-ethoxycarbonyl-2-vinylcyclopropane 8.79 g (54.9 mmol) of diethyl malonate and 99 mL of toluene were added into a three-necked flask (300 mL), and thereafter, 20.5 mL (52.4 mmol) of a 20% sodium ethoxide ethanol solution was added thereto as a base. The obtained mixture was stirred at room temperature for 0.5 hours. Thereafter, 9.89 g (24.9 mmol) of cis-1,4-di-4-toluenesulfonyloxy-2-butene, which had been obtained by performing the same operations as those in Example 1 and then purifying the obtained compound by silica gel chromatography, was added to the reaction solution. The obtained mixture was stirred at room temperature for 3.5 hours, and thereafter, 59.9 mL of a 1 M sodium hydroxide aqueous solution was added to the reaction solution. The obtained mixture was stirred for 1 hour, and an organic layer was then separated. A water layer was re-extracted with 50 mL of toluene, and organic layers were gathered. The gathered organic layer was washed with 50 mL of water three times, and the resultant was then filtrated, while washing the residue with toluene. The obtained filtrate was concentrated at 45° C. under reduced pressure, so as to obtain 22.4 g of 1,1-di-ethoxycarbonyl-2-vinylcyclopropane in the form of a crude product of a light yellow oily substance. This crude product contained 1.25 g of 1,1-di-ethoxycarbonyl-2-vinylcyclopropane (yield: 24%) and 3.94 g of 1,1-di-ethoxy-carbonyl-3-vinylcyclopentene (yield: 74%).

The invention claimed is:

1. A method for producing a compound represented by the following formula (4):

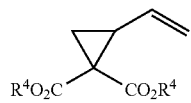  (4)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted, wherein the method comprises a step (i) of allowing a compound represented by the following formula (3):

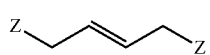  (3)

wherein Z represents a halogen atom or $OR^3$, wherein $R^3$ represents an arylsulfonyl group containing 6 to 12 carbon atoms, an alkylsulfonyl group containing 1 to 10 carbon atoms or an aralkylsulfonyl group containing 7 to 20 carbon atoms, each of which may be optionally substituted,
to react with a malonic ester in the presence of an alkali metal alkoxide or alkali metal hydride, to produce the compound represented by the formula (4),
wherein, in the step (i), the alkali metal alkoxide or alkali metal hydride is used in an amount of 1.5 equivalents or more with respect to 1 equivalent of the compound represented by the above formula (3), and the malonic ester is used in an amount of 1 equivalent or more with respect to 1 equivalent of the alkali metal alkoxide or alkali metal hydride.

2. The method according to claim 1, which further comprises, before the step (i),
a step (ii) of hydrolyzing, with an acid or a base, a compound represented by the following formula (1):

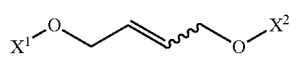  (1)

wherein $X^1$ represents a hydrogen atom or $R^1$, and $X^2$ represents a hydrogen atom or $R^2$, wherein $R^1$ and $R^2$ each independently represent an alkylcarbonyl group containing 2 to 11 carbon atoms, an aralkylcarbonyl group containing 8 to 21 carbon atoms or an arylcarbonyl group containing 7 to 13 carbon atoms, each of which may be optionally substituted, provided that $X^1$ and $X^2$ do not simultaneously represent hydrogen atoms,
so as to produce a compound represented by the following formula (2):

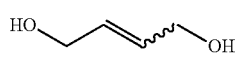  (2)

a step (iii) of allowing the compound represented by the above formula (2), which has been obtained by the above step (ii), to react with a compound represented by $R^3X$ (wherein $R^3$ represents an arylsulfonyl group containing 6 to 12 carbon atoms, an alkylsulfonyl group containing 1 to 10 carbon atoms or an aralkylsulfonyl group containing 7 to 20 carbon atoms, each of which may be optionally substituted; and X represents a halogen atom), so as to produce a compound represented by the following formula (3b):

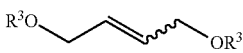

wherein R³ represents an arylsulfonyl group containing 6 to 12 carbon atoms, an alkylsulfonyl group containing 1 to 10 carbon atoms or an aralkylsulfonyl group containing 7 to 20 carbon atoms, each of which may be optionally substituted; and a step (iv) of crystallizing the compound represented by the above formula (3b), which has been obtained by the above step (iii), so as to produce a compound represented by the following (3a):

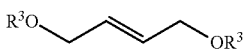

wherein R³ represents an arylsulfonyl group containing 6 to 12 carbon atoms, an alkylsulfonyl group containing 1 to 10 carbon atoms or an aralkylsulfonyl group containing 7 to 20 carbon atoms, each of which may be optionally substituted.

3. The method according to claim 1, which comprises a step of purifying the compound represented by the formula (4) after performing the step (i).

4. A method for producing a compound represented by the following formula (5):

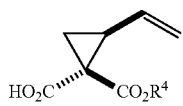

wherein R⁴ represents an alkyl group containing 1 to 10 carbon atoms, an aralkyl group containing 7 to 20 carbon atoms or an aryl group containing 6 to 12 carbon atoms, each of which may be optionally substituted, wherein the method comprises:

a step (v) of producing a compound represented by the following formula (4) by the method according to claim 1:

wherein R⁴ represents an alkyl group containing 1 to 10 carbon atoms, an aralkyl group containing 7 to 20 carbon atoms or an aryl group containing 6 to 12 carbon atoms, each of which may be optionally substituted; and a step (vi) of subjecting the compound represented by the above formula (4), which has been obtained by the above step (v), to hydrolysis, or to hydrolysis and optical resolution, to produce the compound represented by the formula (5).

5. The method according to claim 4, wherein the step (vi) is a step (vi-1) of allowing the compound represented by the formula (4), which has been obtained by the step (v), to react with an enzyme, cells containing the enzyme, a preparation of the cells, or a culture solution obtained by culturing the cells, so as to produce an optically active compound represented by the formula (5).

6. The method according to claim 4, wherein the step (vi) is a step (vi-2) of hydrolyzing the compound represented by the formula (4) obtained by the step (v) to produce a compound represented by the following formula (5a):

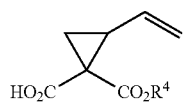

wherein R⁴ represents an alkyl group containing 1 to 10 carbon atoms, an aralkyl group containing 7 to 20 carbon atoms or an aryl group containing 6 to 12 carbon atoms, each of which may be optionally substituted, and then subjecting the compound represented by the formula (5a) to optical resolution using an enzyme, cells containing the enzyme, a preparation of the cells, or a culture solution obtained by culturing the cells, or to optical resolution using an optically active basic compound or by chromatography, to produce an optically active compound represented by the formula (5).

7. The method according to claim 4, wherein the step (vi) is a step (vi-3) of subjecting the compound represented by the formula (4) obtained by the step (v) to optical resolution using an enzyme, cells containing the enzyme, a preparation of the cells, or a culture solution obtained by culturing the cells, or to optical resolution by chromatography, to produce a compound represented by the following formula (4a):

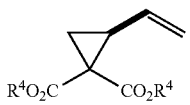

wherein R⁴ represents an alkyl group containing 1 to 10 carbon atoms, an aralkyl group containing 7 to 20 carbon atoms or an aryl group containing 6 to 12 carbon atoms, each of which may be optionally substituted, and then hydrolyzing the compound represented by the formula (4a), to produce an optically active compound represented by the formula (5).

8. The method according to claim 4, wherein the absolute stereochemistry of the compound represented by the formula (5) is (1S,2S).

9. A method for producing a compound represented by the following formula (7):

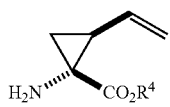

wherein R⁴ represents an alkyl group containing 1 to 10 carbon atoms, an aralkyl group containing 7 to 20 carbon atoms, or an aryl group containing 6 to 12 carbon atoms, each of which may be optionally substituted, or by the following formula (8):

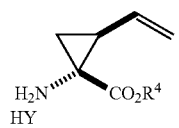

(8)

wherein $R^4$ represents an alkyl group containing 1 to 10 carbon atoms, an aralkyl group containing 7 to 20 carbon atoms, or an aryl group containing 6 to 12 carbon atoms, each of which may be optionally substituted; and HY represents an inorganic acid, sulfonic acid, or carboxylic acid, wherein the method comprises:

a step (vi) of producing a compound represented by the following formula (5) by the method according to claim 4:

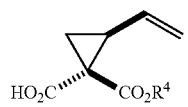

(5)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted;

a step (vii), in which (vii-1) the compound represented by the formula (5) obtained by the above step (vi) is allowed to react with a condensation agent or an acid halogenating agent to obtain a reaction intermediate, and the reaction intermediate is then allowed to react with a metal azide compound or a trialkylsilyl azide, or (vii-2) the compound represented by the formula (5) obtained by the above step (vi) is allowed to react with a phosphoric acid ester-azide, so as to obtain an acid azide, and the acid azide is then converted to an isocyanate, and the isocyanate is further allowed to react with an alcohol, thereby producing a compound represented by the following formula (6):

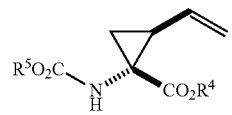

(6)

wherein $R^4$ and $R^5$ each independently represent an alkyl group containing 1 to 10 carbon atoms, an aralkyl group containing 7 to 20 carbon atoms, or an aryl group containing 6 to 12 carbon atoms, each of which may be optionally substituted; and a step (viii) of allowing the compound represented by the above formula (6) obtained by the above step (vii) to react with an acid or a base, or subjecting the compound represented by the formula (6) to a catalytic hydrogenation reaction, so as to produce the compound represented by the formula (7) or the formula (8).

10. The method according to claim 9, wherein, in the step (vii-1), the reaction intermediate is allowed to react with a metal azide compound or a trialkylsilyl azide in the presence of an acid.

11. The method according to claim 9, wherein the absolute stereochemistry of the compound represented by the formula (5) is (1S,2S), and the absolute stereochemistry of each of the compounds represented by the formula (6), the formula (7) and the formula (8) is (1R,2S).

12. A method for producing a compound represented by the following formula (7):

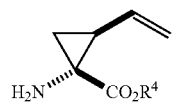

(7)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted, or by the following formula (8):

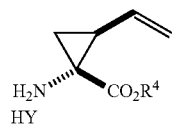

(8)

wherein $R^4$ represents an alkyl group containing 1 to 10 carbon atoms, an aralkyl group containing 7 to 20 carbon atoms, or an aryl group containing 6 to 12 carbon atoms, each of which may be optionally substituted; and HY represents an inorganic acid, sulfonic acid, or carboxylic acid, wherein the method comprises:

a step (vi) of producing a compound represented by the following formula (5) by the method according to claim 4:

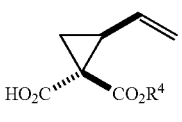

(5)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted; and a step (ix), in which (ix-1) the compound represented by the formula (5) obtained by the above step (vi) is allowed to react with a condensation agent or an acid halogenating agent to obtain a reaction intermediate, and the reaction intermediate is then allowed to react with a metal azide compound or a trialkylsilyl azide, or (ix-2) the compound represented by the formula (5) obtained by the above step (vi) is allowed to react with a phosphoric acid ester-azide, so as to obtain an acid azide, and the acid azide is then converted to an isocyanate, and the isocyanate is further allowed to react with water in the presence of an acid, thereby producing the compound represented by the formula (7) or the formula (8).

13. The method according to claim 12, wherein, in the step (ix-1), the reaction intermediate is allowed to react with a metal azide compound or a trialkylsilyl azide in the presence of an acid.

14. The method according to claim 12, wherein the absolute stereochemistry of the compound represented by the formula (5) is (1S,2S), and the absolute stereochemistry of each of the compounds represented by the formula (7) and the formula (8) is (1R,2S).

15. A method for producing a compound represented by the following formula (7):

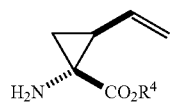

(7)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted, wherein the method comprises:

a step (x) of producing a compound represented by the following formula (8) by the method according to claim 9:

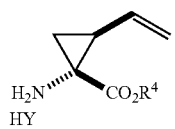

(8)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted; and HY represents an inorganic acid, sulfonic acid, or carboxylic acid; and a step (xi) of allowing the compound represented by the formula (8) obtained by the above step (x) to react with a base.

16. A method for producing a compound represented by the following formula (8):

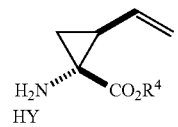

(8)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted; and HY represents an inorganic acid, sulfonic acid, or carboxylic acid, wherein the method comprises:

a step (xii) of producing a compound represented by the following formula (7) by the method according to claim 9:

(7)

wherein $R^4$ represents an alkyl group containing 1 to 10 carbon atoms, an aralkyl group containing 7 to 20 carbon atoms or an aryl group containing 6 to 12 carbon atoms, each of which may be optionally substituted; and a step (xiii) of allowing the compound represented by the formula (7) obtained by the above step (xii) to react with an inorganic acid, sulfonic acid, or carboxylic acid.

17. The method according to claim 16, wherein the step (xiii) is a step of allowing the compound represented by the formula (7) obtained by the above step (xii) to react with sulfuric acid in the presence of an organic solvent.

18. The method according to claim 9, which comprises a step of recrystallizing the compound represented by the formula (8).

* * * * *

```
                        SEQUENCE LISTING

<160> NUMBER OF SEQ ID NOS: 16

<210> SEQ ID NO 1
<211> LENGTH: 489
<212> TYPE: PRT
<213> ORGANISM: Bacillus subtilis

<400> SEQUENCE: 1

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Ser Ile Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Lys Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asn Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ser Ala Ala Phe Leu Gln Val Leu Gly Ile Asn
225                 230                 235                 240

Glu Gly Gln Leu Asp Lys Leu His Thr Val Ser Ala Glu Asp Leu Leu
                245                 250                 255
```

```
Lys Ala Ala Asp Gln Leu Arg Ile Ala Glu Lys Glu Asn Ile Phe Gln
             260                 265                 270
Leu Phe Phe Gln Pro Ala Leu Asp Pro Lys Thr Leu Pro Glu Glu Pro
         275                 280                 285
Glu Lys Ala Ile Ala Glu Gly Ala Ala Ser Gly Ile Pro Leu Leu Ile
     290                 295                 300
Gly Thr Thr Arg Asp Glu Gly Tyr Leu Phe Phe Thr Pro Asp Ser Asp
305                 310                 315                 320
Val His Ser Gln Glu Thr Leu Asp Ala Ala Leu Glu Tyr Leu Leu Gly
                 325                 330                 335
Lys Pro Leu Ala Glu Lys Val Ala Asp Leu Tyr Pro Arg Ser Leu Glu
             340                 345                 350
Ser Gln Ile His Met Met Thr Asp Leu Leu Phe Trp Arg Pro Ala Val
         355                 360                 365
Ala Tyr Ala Ser Ala Gln Ser His Tyr Ala Pro Val Trp Met Tyr Arg
     370                 375                 380
Phe Asp Trp His Pro Lys Lys Pro Pro Tyr Asn Lys Ala Phe His Ala
385                 390                 395                 400
Leu Glu Leu Pro Phe Val Phe Gly Asn Leu Asp Gly Leu Glu Arg Met
                 405                 410                 415
Ala Lys Ala Glu Ile Thr Asp Glu Val Lys Gln Leu Ser His Thr Ile
             420                 425                 430
Gln Ser Ala Trp Ile Thr Phe Ala Lys Thr Gly Asn Pro Ser Thr Glu
         435                 440                 445
Ala Val Asn Trp Pro Ala Tyr His Glu Glu Thr Arg Glu Thr Leu Ile
     450                 455                 460
Leu Asp Ser Glu Ile Thr Ile Glu Asn Asp Pro Glu Ser Glu Lys Arg
465                 470                 475                 480
Gln Lys Leu Phe Pro Ser Lys Gly Glu
                 485

<210> SEQ ID NO 2
<211> LENGTH: 1470
<212> TYPE: DNA
<213> ORGANISM: Bacillus subtilis

<400> SEQUENCE: 2
atgactcatc aaatagtaac gactcaatac ggcaaagtaa aaggcacaac ggaaaacggc      60
gtacataagt ggaaaggcat ccctatgcc aagccgcctg tcggacaatg cgttttaaa      120 gcacctgagc cgcctgaagt gtgggaagat gtgcttgatg ccacagcgta cggctctatt     180
tgcccgcagc cgtctgattt gctgtcactt tcgtatactg agctgccccg ccagtccgag     240
gattgcttgt atgtcaatgt atttgcgcct gacaccccaa gtaaaaatct tcctgtcatg     300
gtgtggattc acggaggcgc tttttatcta ggagcgggca gtgagccatt gtatgacgga     360
tcaaaacttg cggcacaggg agaagtcatt gtcgttacat gaactatcg gctggggccg     420 tttggctttt tgcacttgtc ttcatttaat gaggcgtatt ctgataacct gggcttttta    480
gaccaagccg ccgcgctgaa atgggtgcga gagaatattt cagcgtttgg cggtgatccc     540
gataacgtaa cagtatttgg agaatccgcc ggcgggatga gcattgccgc gctgcttgct    600
atgcctgcgg caaaaggcct gttccagaaa gcaatcatgg aaagcggcgc ttctcgaacg    660
atgacgaaag aacaagcggc gagcacctcg gcagcctttt tacaggtcct tgggattaac    720
gagggccaac tggataaatt gcatacggtt tctgcggaag atttgctaaa agcggctgat    780
```

```
cagcttcgga ttgcagaaaa agaaaatatc tttcagctgt tcttccagcc cgcccttgat   840
ccgaaaacgc tgcctgaaga accagaaaaa gcgatcgcag aaggggctgc ttccggtatt   900
ccgctattaa ttggaacaac ccgtgatgaa ggatatttat ttttcacccc ggattcagac   960
gttcattctc aggaaacgct tgatgcagcg ctcgagtatt tactagggaa gccgctggca  1020
gagaaagttg ccgatttgta tccgcgttct ctggaaagcc aaattcatat gatgactgat  1080
ttattatttt ggcgccctgc cgtcgccat gcatccgcac agtctcatta cgcccctgtc  1140
tggatgtaca ggttcgattg gcacccgaag aagccgccgt acaataaagc gtttcacgca  1200
ttagagcttc cttttgtctt tggaaatctg gacggattgg aacgaatggc aaaagcggag  1260
attacggatg aggtgaaaca gctttctcac acgatacaat cagcgtggat cacgttcgcc  1320
aaaacaggaa acccaagcac cgaagctgtg aattggcctg cgtatcatga gaaaacgaga  1380
gagacgctga ttttagactc agagattacg atcgaaaacg atcccgaatc tgaaaaaagg  1440
cagaagctat tcccttcaaa aggagaataa                                   1470
```

```
<210> SEQ ID NO 3
<211> LENGTH: 33
<212> TYPE: DNA
<213> ORGANISM: Artificial
<220> FEATURE:
<223> OTHER INFORMATION: PCR primer

<400> SEQUENCE: 3
gcgaattcat gactcatcaa atagtaacga ctc                                33

<210> SEQ ID NO 4
<211> LENGTH: 33
<212> TYPE: DNA
<213> ORGANISM: Artificial
<220> FEATURE:
<223> OTHER INFORMATION: PCR primer

<400> SEQUENCE: 4
gctctagatt attctccttt tgaagggaat agc                                33

<210> SEQ ID NO 5
<211> LENGTH: 32
<212> TYPE: DNA
<213> ORGANISM: Artificial
<220> FEATURE:
<223> OTHER INFORMATION: PCR primer

<400> SEQUENCE: 5
tcccccgggg tcaaggcgca ctcccgttct gg                                 32

<210> SEQ ID NO 6
<211> LENGTH: 35
<212> TYPE: DNA
<213> ORGANISM: Artificial
<220> FEATURE:
<223> OTHER INFORMATION: PCR primer

<400> SEQUENCE: 6
tcccccgggg tggggtgcct aatgagtgag ctaac                              35

<210> SEQ ID NO 7
<211> LENGTH: 1470
<212> TYPE: DNA
<213> ORGANISM: Bacillus subtilis
```

<400> SEQUENCE: 7

```
atgactcatc aaatagtaac gactcaatac ggcaaagtaa aaggcacaac agaaaatggc    60
gtacataaat ggaaaggcat cccctatgcc agaccgcctg tcgggccatt gcgttttaaa   120
gcaccggaac ctccggaagc gtgggagaac gaactggacg caacagcgta cggccctatt   180
tgcccgcagc cgtctgattt gctgtcactt tcgtataatg agctgccccg ccagtctgag   240
aattgcttgt atgtcaatgt atttgcgcct gatactccaa gtcaaaacct gcctgtcatg   300
gtgtggattc acggcggcgc ttttttatctt ggagcgggca gtgagccatt attcgatggg   360
tcaagacttg cggcgcaggg agaagtcatt gtcgttacac tgaattatcg actggggccg   420
tttggatttt tacatttgtc ttcgtttgat gaggcgtatt ccgataacct tggtcttttg   480
gaccaagccg ccgcactgaa atgggtgcga gacaatatct cagcatttgg cggtgatccg   540
gataacgtaa cggtatttgg agaatccgct ggcggcatga gcattgccgc gctgctcgca   600
atgcctgcgg caaaaggcct gttccagaaa gcgatcatgg aaagcggcgc ttctagaaca   660
atgacaacag aaaaagcggc tagcactgca gcagcctttt tacaggtcct tgggattaac   720
gagagccaat tggacagact gcacactgta tctgcggaag atttgcttaa agcggccgat   780
aagcttcgga aagcagaaaa tgaaaatctc tttcagctgt tattccagcc cgcccttgat   840
ccgaaaacgc tgcctgctga accagaaaaa gcaatcgcag gaggtgctgc tgccgacatt   900
ccgctgttaa tcggaacaaa ccgcgatgaa ggatatttat ttttcacccc ggactcagac   960
gttcattctc aagaaacgtt taatgccgcg cttgagtatt tattggaaca gccgctggca  1020
aagaaagccg ccgatctgta tccgcgttca ctagaaagcc aaattcatat gatgactgat  1080
ttgttatttt ggcgcccggc cgtcgcctat gcctccgctc agtctcaata cgcgcctgta  1140
tggatgtacc gatttgattg gcactctgat aagccgccat acaataaggc gtttcacgca  1200
ttagagcttc cttttgttt cggaaatctg gacgggttag aacgaatggc aaaagcagag  1260
gttacggatg aggtgaaacg gctttctcat accatacaat cagcatggat cacgtttgcc  1320
aaaacaggaa acccaagcac cgaagatgta aaatggccgg cgtatcatga gaaacaaga   1380
cagacgctga тттагатtс agagattacg atcgaaaacg atcctgaatc tgaaaaaagg  1440
cagaagctat tcccttcaaa aggagaataa                                   1470
```

<210> SEQ ID NO 8
<211> LENGTH: 489
<212> TYPE: PRT
<213> ORGANISM: Bacillus subtilis

<400> SEQUENCE: 8

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Arg Pro
            20                  25                  30

Pro Val Gly Pro Leu Arg Phe Lys Ala Pro Glu Pro Glu Ala Trp
        35                  40                  45

Glu Asn Glu Leu Asp Ala Thr Ala Tyr Gly Pro Ile Cys Pro Gln Pro
    50                  55                  60

Ser Asp Leu Leu Ser Leu Ser Tyr Asn Glu Leu Pro Arg Gln Ser Glu
65                  70                  75                  80

Asn Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
```

```
              100                 105                 110
Gly Ser Glu Pro Leu Phe Asp Gly Ser Arg Leu Ala Gln Gly Glu
            115                 120                 125

Val Ile Val Val Thr Leu Asn Tyr Arg Leu Gly Pro Phe Gly Phe Leu
            130                 135             140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Asp Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
            195                 200                 205

Gln Lys Ala Ile Met Glu Ser Gly Ala Ser Arg Thr Met Thr Thr Glu
            210                 215                 220

Lys Ala Ala Ser Thr Ala Ala Ala Phe Leu Gln Val Leu Gly Ile Asn
225                 230                 235                 240

Glu Ser Gln Leu Asp Arg Leu His Thr Val Ser Ala Glu Asp Leu Leu
                245                 250                 255

Lys Ala Ala Asp Lys Leu Arg Lys Ala Glu Asn Glu Asn Leu Phe Gln
            260                 265                 270

Leu Leu Phe Gln Pro Ala Leu Asp Pro Lys Thr Leu Pro Ala Glu Pro
            275                 280                 285

Glu Lys Ala Ile Ala Gly Gly Ala Ala Ala Asp Ile Pro Leu Leu Ile
            290                 295                 300

Gly Thr Asn Arg Asp Glu Gly Tyr Leu Phe Phe Thr Pro Asp Ser Asp
305                 310                 315                 320

Val His Ser Gln Glu Thr Phe Asn Ala Ala Leu Glu Tyr Leu Leu Glu
                325                 330                 335

Gln Pro Leu Ala Lys Lys Ala Ala Asp Leu Tyr Pro Arg Ser Leu Glu
            340                 345                 350

Ser Gln Ile His Met Met Thr Asp Leu Leu Phe Trp Arg Pro Ala Val
            355                 360                 365

Ala Tyr Ala Ser Ala Gln Ser Gln Tyr Ala Pro Val Trp Met Tyr Arg
            370                 375                 380

Phe Asp Trp His Ser Asp Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Val Thr Asp Glu Val Lys Arg Leu Ser His Thr Ile
            420                 425                 430

Gln Ser Ala Trp Ile Thr Phe Ala Lys Thr Gly Asn Pro Ser Thr Glu
            435                 440                 445

Asp Val Lys Trp Pro Ala Tyr His Glu Glu Thr Arg Gln Thr Leu Ile
            450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
            485

<210> SEQ ID NO 9
<211> LENGTH: 40
<212> TYPE: DNA
<213> ORGANISM: Artificial
```

<220> FEATURE:
<223> OTHER INFORMATION: PCR primer
<220> FEATURE:
<221> NAME/KEY: misc_feature
<222> LOCATION: (19)..(20)
<223> OTHER INFORMATION: n; A, T, G or C

<400> SEQUENCE: 9
ccgtctgatt tgctgtcann ktcgtataat gagctgcccc                40

<210> SEQ ID NO 10
<211> LENGTH: 40
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (21)..(22)
<223> OTHER INFORMATION: n; A, T, G or C

<400> SEQUENCE: 10
ggggcagctc attatacgam nntgacagca aatcagacgg                40

<210> SEQ ID NO 11
<211> LENGTH: 32
<212> TYPE: DNA
<213> ORGANISM: Artificial
<220> FEATURE:
<223> OTHER INFORMATION: PCR primer
<220> FEATURE:
<221> NAME/KEY: misc_feature
<223> OTHER INFORMATION: n; A, T, G or C
<220> FEATURE:
<221> NAME/KEY: misc_feature
<222> LOCATION: (17)..(18)
<223> OTHER INFORMATION: n; A, T, G or C

<400> SEQUENCE: 11
ccgcgatgaa ggatatnnkt ttttcacccc gg                        32

<210> SEQ ID NO 12
<211> LENGTH: 32
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (15)..(16)
<223> OTHER INFORMATION: n; A, T, G or C

<400> SEQUENCE: 12
ccggggtgaa aaamnnatat ccttcatcgc gg                        32

<210> SEQ ID NO 13
<211> LENGTH: 53
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (26)..(27)
<223> OTHER INFORMATION: n; A, T, G or C
<220> FEATURE:
<221> NAME/KEY: misc_feature
<222> LOCATION: (35)..(36)
<223> OTHER INFORMATION: n; A, T, G or C

<400> SEQUENCE: 13
gcttcggaaa gcagaaaatg aaaatnnktt tcagnnktta ttccagcccg ccc    53

<210> SEQ ID NO 14
<211> LENGTH: 53
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (18)..(19)
<223> OTHER INFORMATION: n; A, T, G or C
<220> FEATURE:
<221> NAME/KEY: misc_feature
<222> LOCATION: (27)..(28)
<223> OTHER INFORMATION: n; A, T, G or C

<400> SEQUENCE: 14
gggcgggctg gaataamnnc tgaaamnnat tttcattttc tgctttccga agc    53

<210> SEQ ID NO 15
<211> LENGTH: 1470
<212> TYPE: DNA
<213> ORGANISM: Bacillus subtilis

<400> SEQUENCE: 15
atgactcatc aaatagtaac gactcaatac ggcaaagtaa aaggcacaac agaaaatggc     60
gtacataaat ggaaaggcat cccctatgcc agaccgcctg tcgggccatt gcgttttaaa    120
gcaccggagc ctccggaagc gtgggagaac gaactggacg caacagcgta cggccctatt    180
tgcccgcagc cgtctgattt gctgtcagat tcgtataatg agctgccccg ccagtctgag    240
aattgcttgt atgtcaatgt atttgcgcct gatactccaa gtcaaaacct gcctgtcatg    300
gtgtggattc acggcggcgc ttttatctt ggagcgggca gtgagccatt attcgatggg    360
tcaagacttg cggcgcaggg agaagtcatt gtcgttacac tgaattatcg actggggccg    420
tttggatttt tacatttgtc ttcgtttgat gaggcgtatt ccgataacct tggtcttttg    480
gaccaagccg ccgcactgaa atgggtgcga gacaatatct cagcatttgg cggtgatccg    540
gataacgtaa cggtatttgg agaatccgct ggcggcatga gcattgccgc gctgctcgca    600
atgcctgcgg caaaaggcct gttccagaaa gcgatcatgg aaagcggcgc ttctagaaca    660
atgacaacag aaaaagcggc tagcactgca gcagcctttt tacaggtcct ggggattaac    720
gagagccaat ggacagact gcacactgta tctgcggaag atttgcttaa agcggccgat    780
aagcttcgga aagcagaaaa tgaaaatcag tttcagcggt tattccagcc cgcccttgat    840
ccgaaaacgc tgcctgctga accagaaaaa gcaatcgcag gaggtgctgc tgccgacatt    900
ccgctgttaa tcggaacaaa ccgcgatgaa ggatatatgt ttttcacccc ggactcagac    960
gttcattctc aagaaacgtt taatgccgcg cttgagtatt tattggaaca gccgctggca   1020
aagaaagccg ccgatctgta tccgcgttca ctagaaagcc aaattcatat gatgactgat   1080
ttgttatttt ggcgcccggc cgtcgcctat gcctccgctc agtctcaata cgcgcctgta   1140
tggatgtacc gatttgattg gcactctgat aagccgccat acaataaggc gtttcacgca   1200
ttagagcttc cttttgtttt cggaaatctg gacgggttag aacgaatggc aaaagcagag   1260
gttacggatg aggtgaaacg gctttctcat accatacaat cagcatggat cacgtttgcc   1320
aaaacaggaa acccaagcac cgaagatgta aaatggccgg cgtatcatga agaaacaaga   1380
cagacgctga ttttagattc agagattacg atcgaaaacg atcctgaatc tgaaaaaagg   1440
cagaagctat tcccttcaaa aggagaataa                                                  1470

<210> SEQ ID NO 16
<211> LENGTH: 489
<212> TYPE: PRT
<213> ORGANISM: Bacillus subtilis

<400> SEQUENCE: 16

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Arg Pro
            20                  25                  30

Pro Val Gly Pro Leu Arg Phe Lys Ala Pro Glu Pro Pro Glu Ala Trp
        35                  40                  45

Glu Asn Glu Leu Asp Ala Thr Ala Tyr Gly Pro Ile Cys Pro Gln Pro
    50                  55                  60

Ser Asp Leu Leu Ser Asp Ser Tyr Asn Glu Leu Pro Arg Gln Ser Glu
65                  70                  75                  80

Asn Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Phe Asp Gly Ser Arg Leu Ala Ala Gln Gly Glu
        115                 120                 125

Val Ile Val Val Thr Leu Asn Tyr Arg Leu Gly Pro Phe Gly Phe Leu
130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Asp Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Thr Glu
210                 215                 220

Lys Ala Ala Ser Thr Ala Ala Phe Leu Gln Val Leu Gly Ile Asn
225                 230                 235                 240

Glu Ser Gln Leu Asp Arg Leu His Thr Val Ser Ala Glu Asp Leu Leu
                245                 250                 255

Lys Ala Ala Asp Lys Leu Arg Lys Ala Glu Asn Glu Asn Gln Phe Gln
            260                 265                 270

Arg Leu Phe Gln Pro Ala Leu Asp Pro Lys Thr Leu Pro Ala Glu Pro
        275                 280                 285

Glu Lys Ala Ile Ala Gly Gly Ala Ala Ala Asp Ile Pro Leu Leu Ile
290                 295                 300

Gly Thr Asn Arg Asp Glu Gly Tyr Met Phe Phe Thr Pro Asp Ser Asp
305                 310                 315                 320

Val His Ser Gln Glu Thr Phe Asn Ala Ala Leu Glu Tyr Leu Leu Glu
                325                 330                 335

-continued

```
Gln Pro Leu Ala Lys Lys Ala Ala Asp Leu Tyr Pro Arg Ser Leu Glu
            340             345                 350
Ser Gln Ile His Met Met Thr Asp Leu Leu Phe Trp Arg Pro Ala Val
        355             360                 365
Ala Tyr Ala Ser Ala Gln Ser Gln Tyr Ala Pro Val Trp Met Tyr Arg
    370             375             380
Phe Asp Trp His Ser Asp Lys Pro Pro Tyr Asn Lys Ala Phe His Ala
385             390             395             400
Leu Glu Leu Pro Phe Val Phe Gly Asn Leu Asp Gly Leu Glu Arg Met
            405             410             415
Ala Lys Ala Glu Val Thr Asp Glu Val Lys Arg Leu Ser His Thr Ile
            420             425             430
Gln Ser Ala Trp Ile Thr Phe Ala Lys Thr Gly Asn Pro Ser Thr Glu
        435             440             445
Asp Val Lys Trp Pro Ala Tyr His Glu Glu Thr Arg Gln Thr Leu Ile
        450             455             460
Leu Asp Ser Glu Ile Thr Ile Glu Asn Asp Pro Glu Ser Glu Lys Arg
465             470             475             480
Gln Lys Leu Phe Pro Ser Lys Gly Glu
                485
```